United States Patent
Saisho et al.

(10) Patent No.: US 12,048,552 B2
(45) Date of Patent: Jul. 30, 2024

(54) ELECTROMYOGRAPHY PROCESSING APPARATUS, ELECTROMYOGRAPHY PROCESSING METHOD AND ELECTROMYOGRAPHY PROCESSING PROGRAM

(71) Applicant: Nippon Telegraph and Telephone Corporation, Tokyo (JP)

(72) Inventors: Osamu Saisho, Musashino (JP); Shingo Tsukada, Atsugi (JP); Kentaro Tanaka, Musashino (JP); Daigoro Yokozeki, Musashino (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 631 days.

(21) Appl. No.: 17/281,880

(22) PCT Filed: Jul. 18, 2019

(86) PCT No.: PCT/JP2019/028219
§ 371 (c)(1),
(2) Date: Mar. 31, 2021

(87) PCT Pub. No.: WO2020/070949
PCT Pub. Date: Apr. 9, 2020

(65) Prior Publication Data
US 2021/0386358 A1 Dec. 16, 2021

(30) Foreign Application Priority Data

Oct. 5, 2018 (JP) .................................. 2018-190328

(51) Int. Cl.
*A61B 5/397* (2021.01)
*A61B 5/00* (2006.01)
*A61B 5/389* (2021.01)

(52) U.S. Cl.
CPC .............. *A61B 5/397* (2021.01); *A61B 5/389* (2021.01); *A61B 5/7221* (2013.01);
(Continued)

(58) Field of Classification Search
CPC ....... A61B 5/397; A61B 5/389; A61B 5/7221; A61B 5/7275; A61B 5/7282; A61B 2503/10
See application file for complete search history.

(56) References Cited

U.S. PATENT DOCUMENTS

| 6,076,011 A * | 6/2000 | Hoover ................... A61B 5/389 |
| | | 600/546 |
| 6,485,418 B2 | 11/2002 | Yasushi et al. |
| 2001/0039372 A1 | 11/2001 | Yasushi et al. |

FOREIGN PATENT DOCUMENTS

JP 2001-258858 9/2001

OTHER PUBLICATIONS

[No Author Listed], "Shaping the athletic brain!—Sports performance improvement system based on brain science," NTT Communication Science Laboratories, 2016, 2 pages (with English Translation).

(Continued)

*Primary Examiner* — David J. McCrosky
(74) *Attorney, Agent, or Firm* — Fish & Richardson P.C.

(57) ABSTRACT

An electromyography processing apparatus comprises a storage device that stores the electromyography data of the predetermined muscle; and an onset detection unit configured to determine that a portion is an onset portion based on the electromyography of a sliding window for onset detection and a threshold value; wherein the onset detection unit further comprises a threshold value determination unit con- (Continued)

figured to determine the threshold value based on the electromyography of a sliding window for threshold value detection.

8 Claims, 21 Drawing Sheets

(52) U.S. Cl.
CPC .......... *A61B 5/7275* (2013.01); *A61B 5/7282* (2013.01); *A61B 2503/10* (2013.01)

(56) References Cited

OTHER PUBLICATIONS

Hodges et al., "A comparison of computer-based methods for the determination of onset of muscle contraction using electromyography," Electroencephalography and clinical Neurophysiology, 1996, 101:511-519.

Saisho et al., "Practical pedaling skill items extraction for efficient pedaling training with surface EMG wear," Proceedings of the 2018 ACM International Symposium on Wearable Computers—ISWC '18, Singapore, Oct. 2018, pp. 76-79.

* cited by examiner

13 ONSET DATA

| ONSET IDENTIFIER | START TIME | END TIME |
|---|---|---|
| 1 | ..... | ..... |
| 2 | ..... | ..... |
| ..... | ..... | ..... |

14 ON/OFF INDICATOR DATA

| ONSET IDENTIFIER | ON/OFF INDICATOR |
|---|---|
| 1 | ..... |
| 2 | ..... |
| ..... | ..... |

| TIME | MUSCLE IDENTIFIER | BALANCE EVALUATION VALUE |
|---|---|---|
| 1 | 1 | ..... |
|   | 2 | ..... |
|   | 3 | ..... |
|   | ..... | ..... |
| 2 | 1 | ..... |
|   | 2 | ..... |
|   | 3 | ..... |
|   | ..... | ..... |
| ..... | ..... | ..... |

16 BALANCE EVALUATION VALUE DATA

FIG. 7
(a)
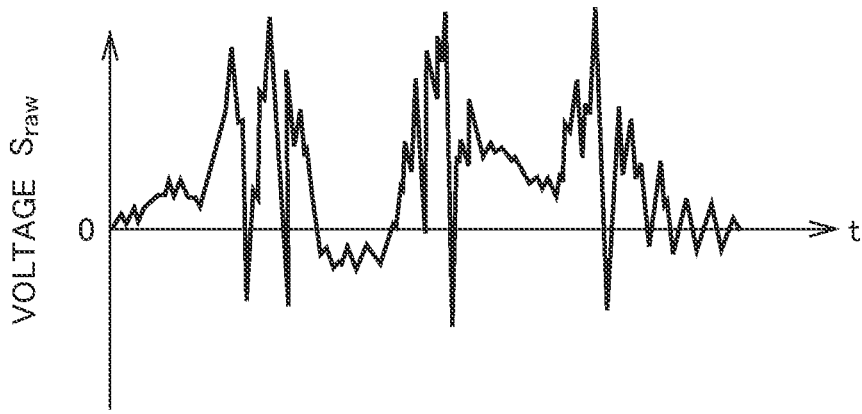
(b)
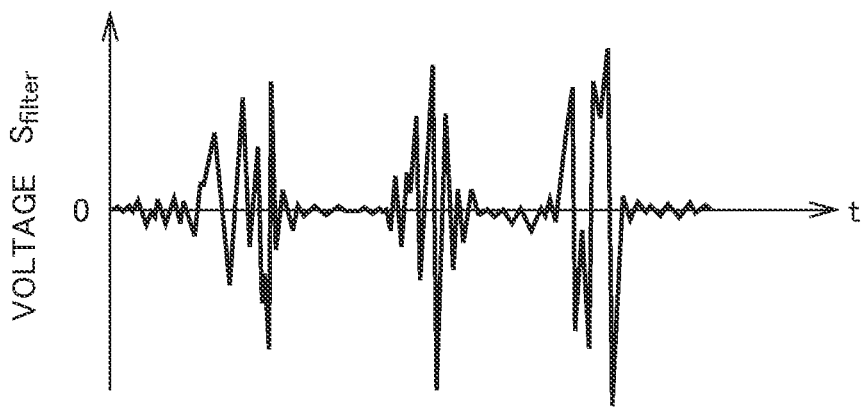
(c)
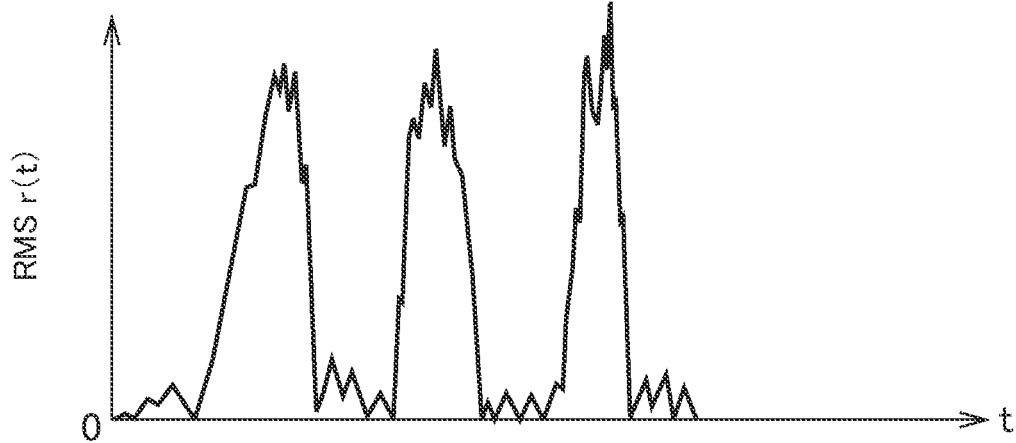

FIG. 10
(a)
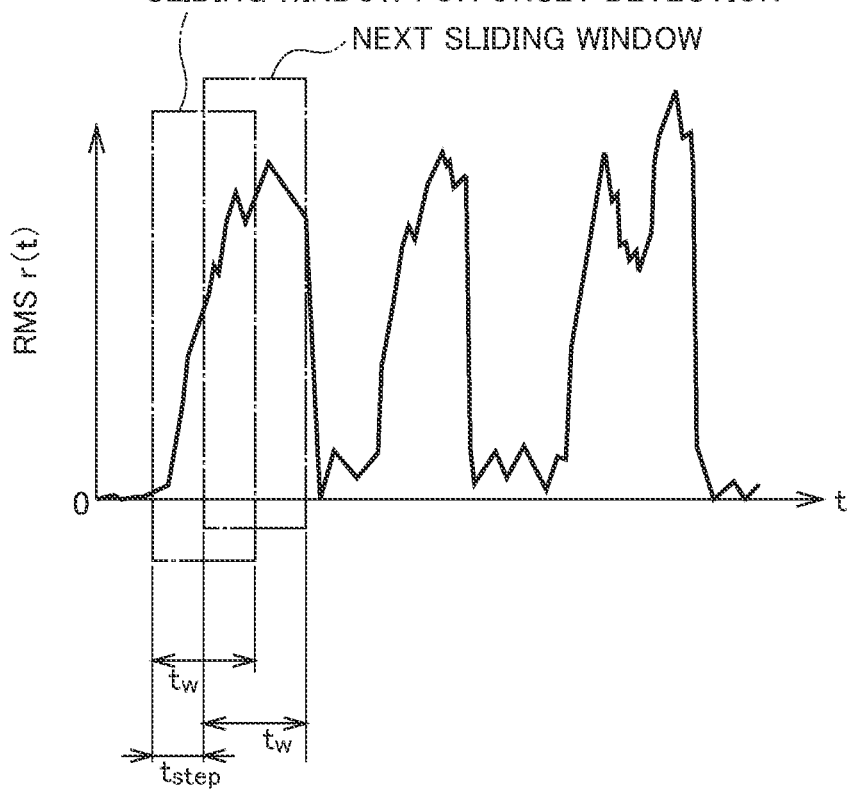
(b)
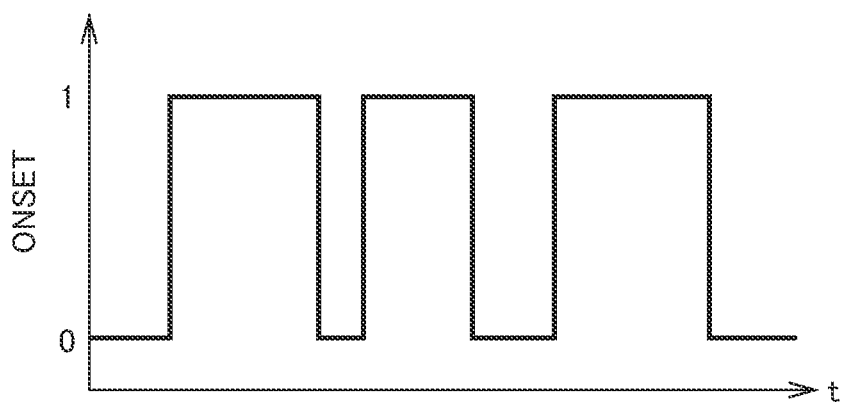

FIG. 13
(a)
WINDOW WITH $t_{w\theta}$ OF SLIDING WINDOW
FOR THRESHOLD VALUE DETERMINATION
WINDOW WITH $t_w$ OF SLIDING WINDOW FOR ONSET DETECTION
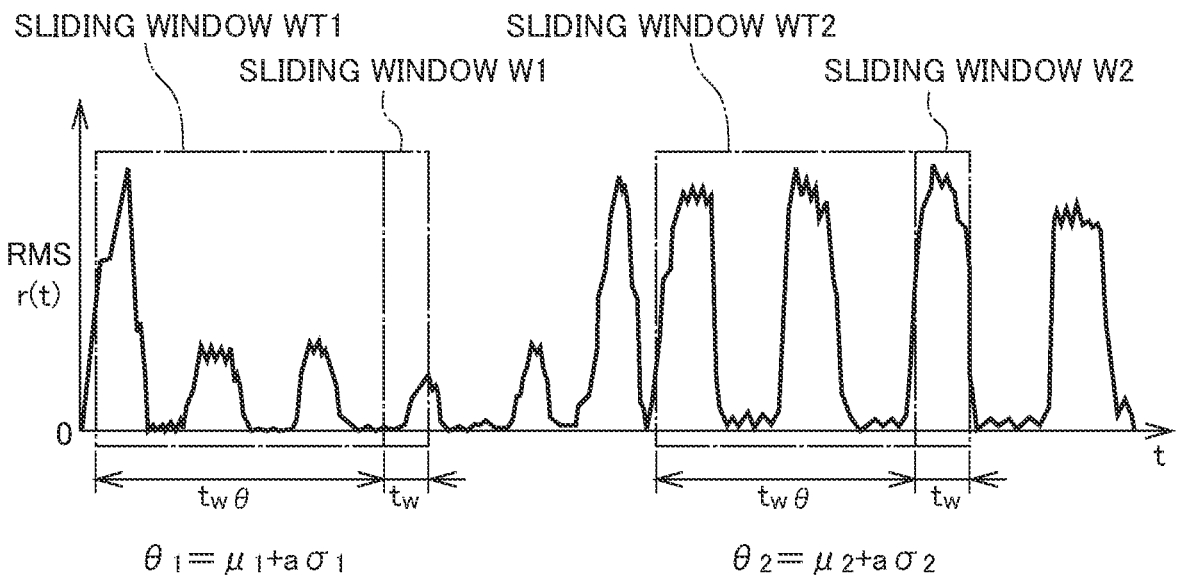
※DETERMINE ONSET SECTION OF　　※DETERMINE ONSET SECTION OF
SLIDING WINDOW W1 BY USING $\theta_1$　SLIDING WINDOW W2 BY USING $\theta_2$
(b)
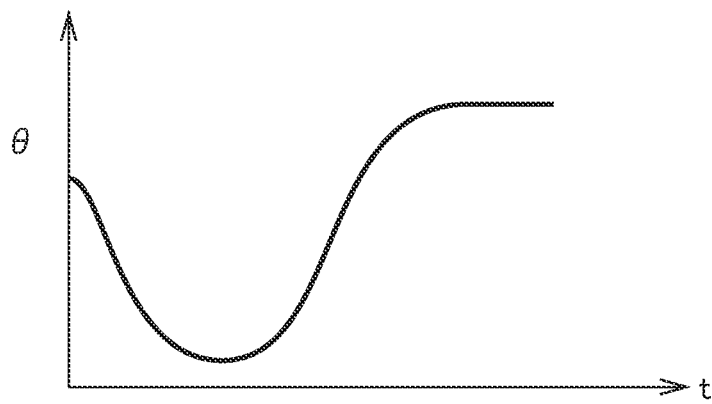

FIG. 14
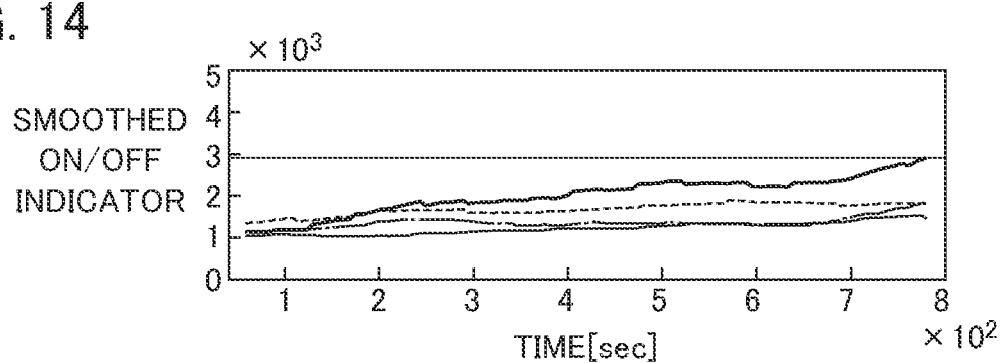
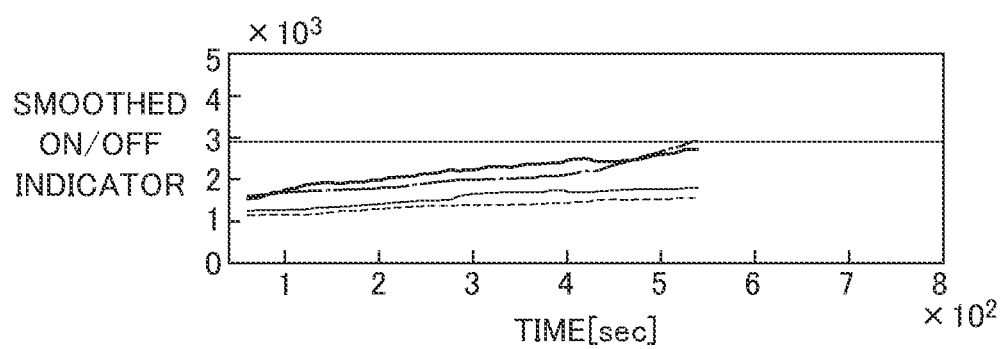
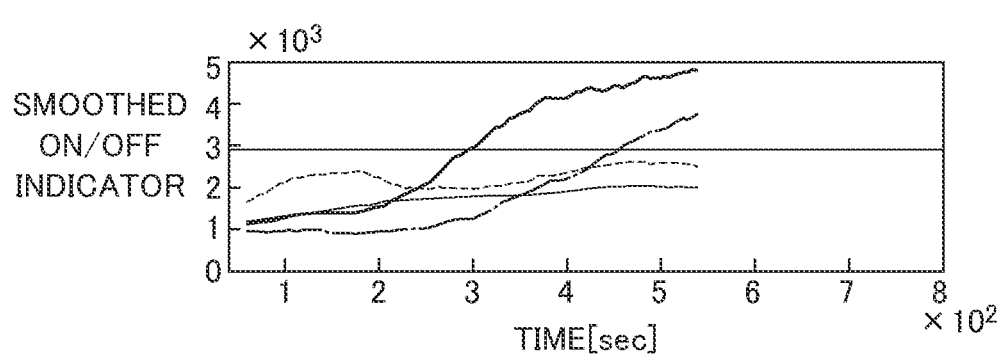
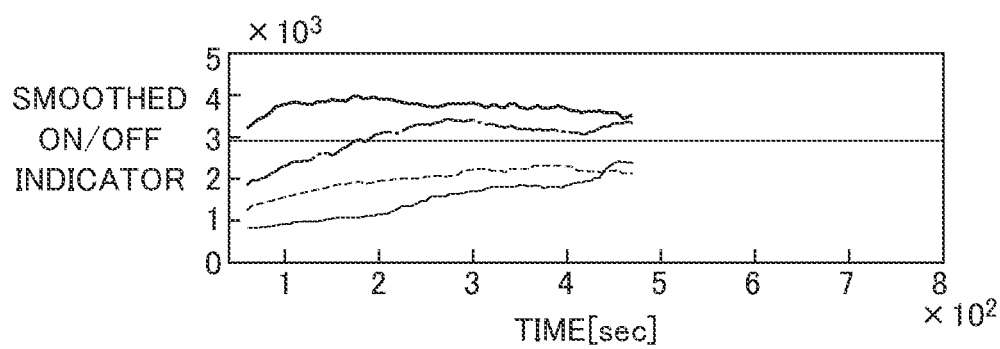

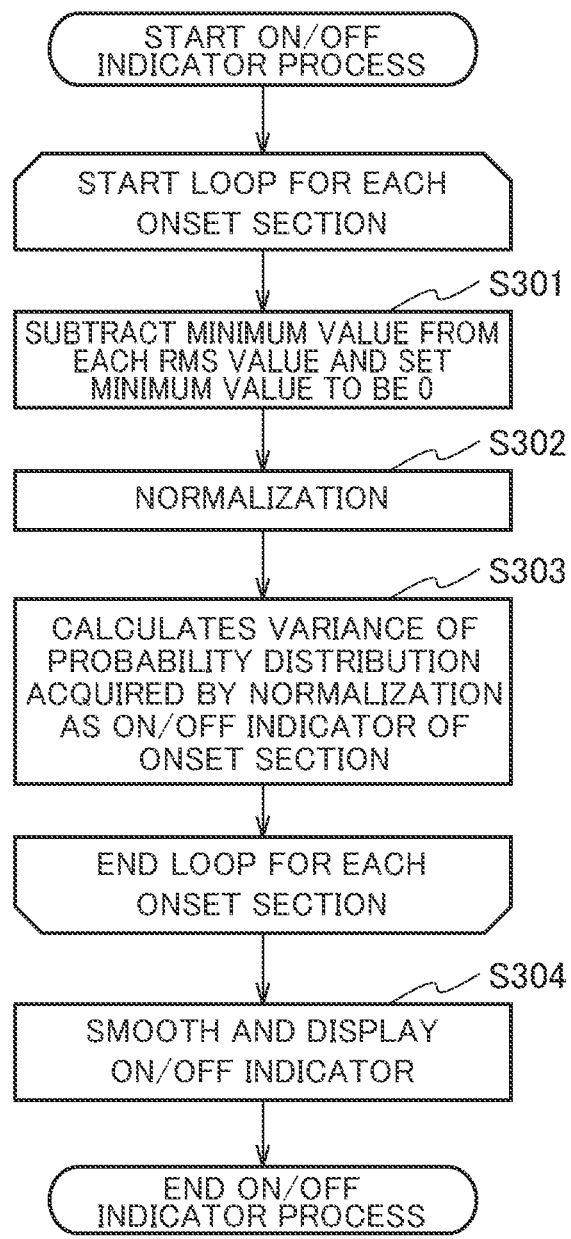

FIG. 16

(a) 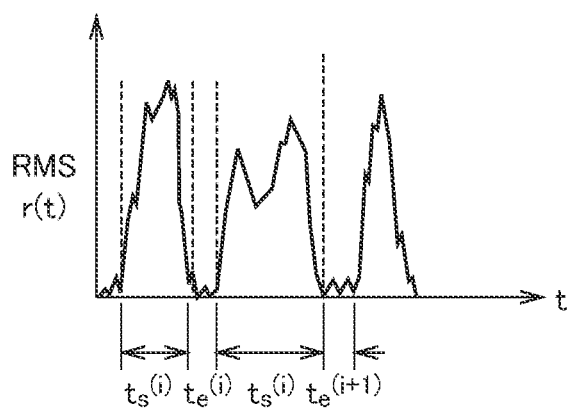

$t_s^{(i)}$ : START TIME OF i-TH ONSET SECTION
$t_e^{(i)}$ : END TIME OF i-TH ONSET SECTION (b)
- MINIMUM RMS $r_{min}^{(i)}$ IN ONSET SECTION
- SUBTRACT $r_{min}^{(i)}$ FROM ENTIRE VALUE TO SET MINIMUM VALUE TO 0
- TO BE REGARDED AS PROBABILITY DISTRIBUTION, DIVIDE VALUE BY $$\sum_{t=t_s^{(i)}}^{t_e^{(i)}} (r(t) - r_{min}^{(i)})$$ , SUM OF r(t) OF WHOLE, SO THAT INTEGRAL OF t BY $[t_s^{(i)}, t_e^{(i)}]$ IS EQUAL TO 1

$$\Rightarrow P(t) = \frac{r(t) - r_{min}^{(i)}}{\sum_{t=t_s^{(i)}}^{t_e^{(i)}} (r(t) - r_{min}^{(i)})}$$

(c) 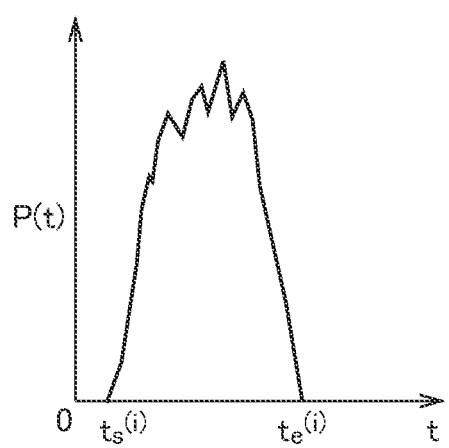

FIG. 17

$I_{te}^{(i)} = \text{Var}(t)$
(FRACTION OF PROBABILITY DISTRIBUTION
P(t) DEFINED IN $[t_s^{(i)}, t_e^{(i)}]$)

FIG. 18
(a)
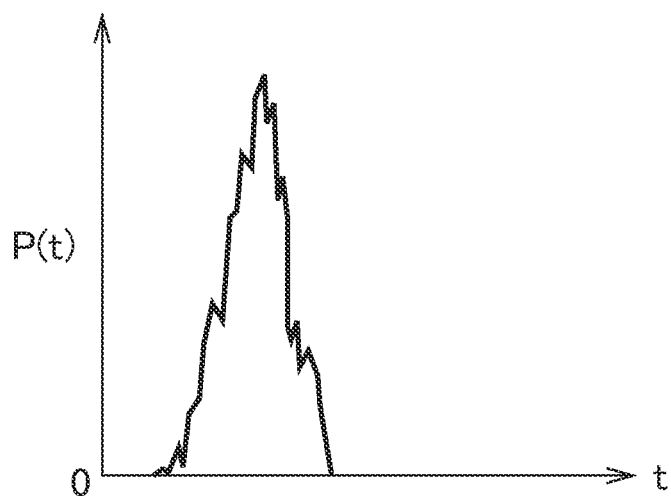
(b)
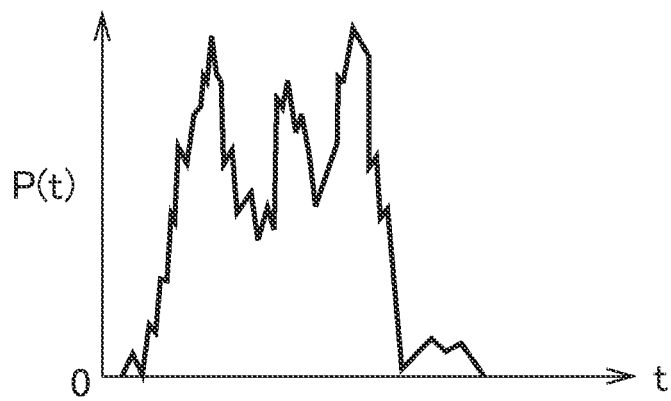
(c)
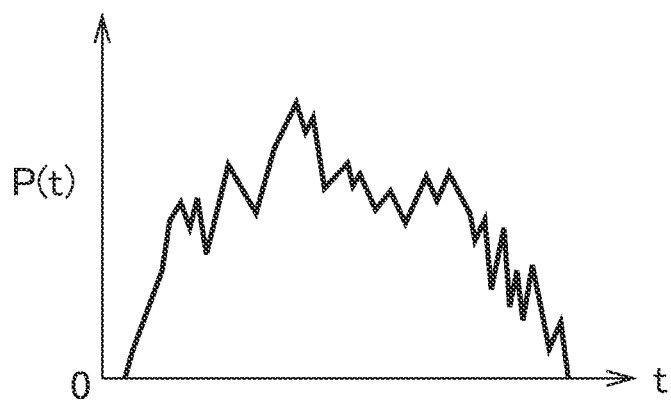

FIG. 19
(a)
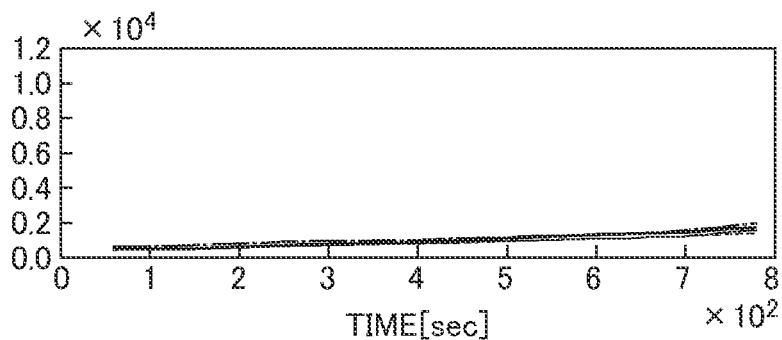
(b)
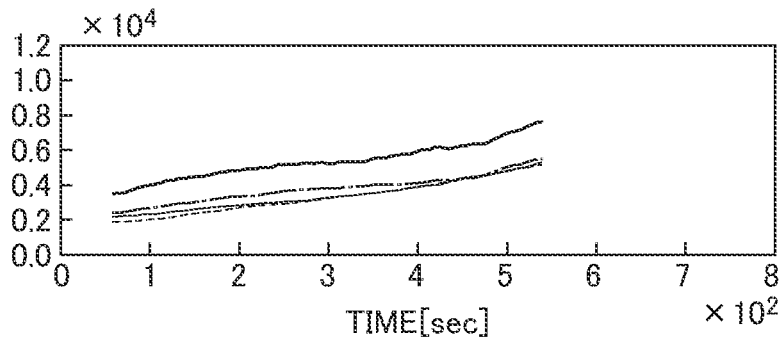
(c)
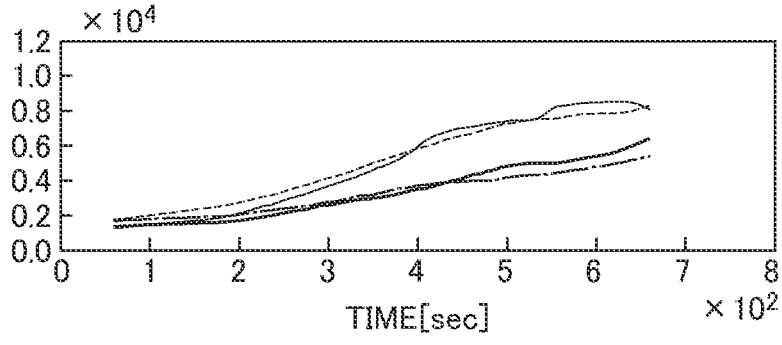
(d)
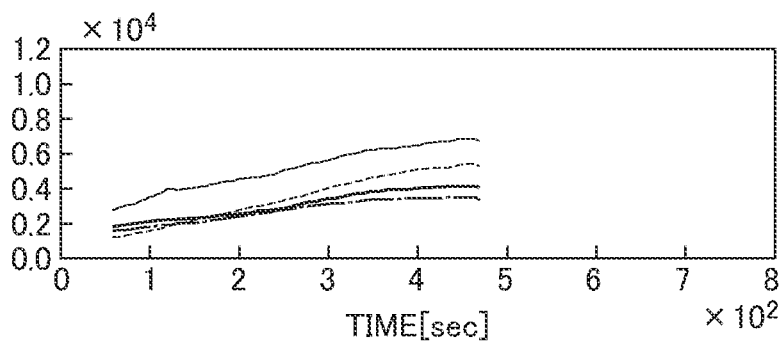
LEGEND ——— VASTUS LATERALIS MUSCLE LEFT ——— VASTUS LATERALIS MUSCLE RIGHT
——— HAMSTRING LEFT ——— HAMSTRING RIGHT FIG. 20
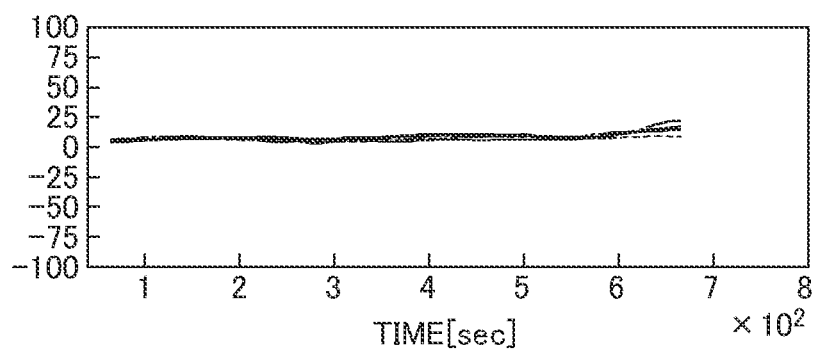
(a)
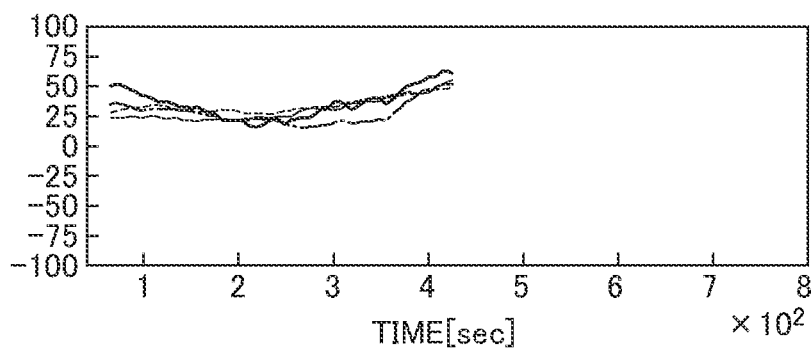
(b)
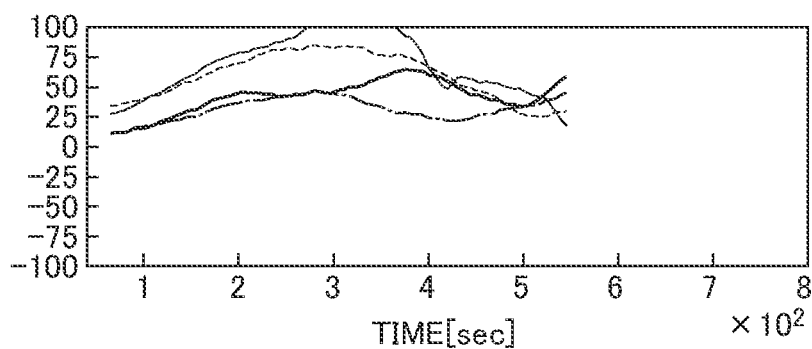
(c)
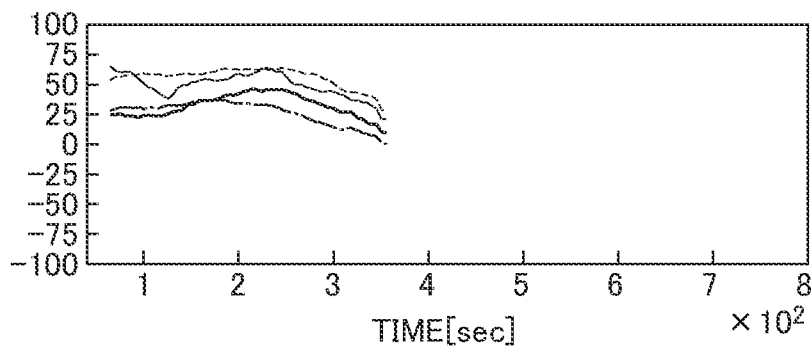
(d)
LEGEND
— VASTUS LATERALIS MUSCLE LEFT
--- VASTUS LATERALIS MUSCLE RIGHT
— HAMSTRING LEFT
-·- HAMSTRING RIGHT IF MUSCLE TYPE IS SET AS p (p ∈ {A,B,C}),
INDICATOR $b_t$ AS TO WHETHER DEPENDENCY IS
MADE ON PARTICULAR MUSCLE CAN BE
EXPRESSED AS $$b_t = \max_p \Delta \tilde{r}_{(t,p)} - \min_p \Delta \tilde{r}_{(t,p)}$$

$$\begin{pmatrix} b_t \text{ IS LARGE} \rightarrow \text{BAD} \\ b_t \text{ IS SMALL} \rightarrow \text{GOOD} \end{pmatrix}$$

ELECTROMYOGRAPHY PROCESSING APPARATUS, ELECTROMYOGRAPHY PROCESSING METHOD AND ELECTROMYOGRAPHY PROCESSING PROGRAM

CROSS-REFERENCE TO RELATED APPLICATIONS

This application is a National Stage application under 35 U.S.C. § 371 of International Application No. PCT/JP2019/028219, having an International Filing Date of Jul. 18, 2019, which claims priority to Japanese Application Serial No. 2018-190328, filed on Oct. 5, 2018. The disclosure of the prior application is considered part of the disclosure of this application, and is incorporated in its entirety into this application.

TECHNICAL FIELD

The present invention relates to an electromyography processing apparatus, an electromyography processing method, and an electromyography processing program of processing electromyography data indicating a time course of an electromyography acquired from an electrode set to a predetermined muscle of an athlete.

BACKGROUND ART

To improve various sport techniques, the utilization of an electromyography that is physiological information directly expressing how to use a body is attracting attention. The electromyography is a voltage generated when a muscle is moved. The electromyography is also referred to as EMG (electromyography). An amplitude of the electromyography increases when force is applied to the muscle, and alternatively becomes close to zero when the force is removed from the muscle. By focusing on the electromyography, it is expected that an athlete himself/herself interprets whether the muscle is appropriately used in a training ground, and utilizes the interpretation in the training to improve the performance.

However, the electromyography is merely an electric signal, and thus, the interpretation of the electromyography data is difficult, and therefore, a technique is required by which the electromyography data is processed so that the athlete himself/herself can understand the electromyography data. For example, there is a technique in which a timing at which the muscle moves and the electromyography increases for a plurality of muscles is detected, a sound of a frequency applied to each of the muscles is sounded, and a feedback is sent to the athlete with the sound (see Non-patent document 1).

There is also a threshold-based method used to detect an onset section in which force is applied to the muscle when the electromyography data is analyzed (see Non-patent document 2). In Non-patent document 2, data of the electromyography is measured in advance when the athlete is static, and the onset section is detected based on a threshold value determined in accordance with the measured data.

PRIOR ART DOCUMENT

Non-Patent Document

Non-patent document 1: NTT Communication Science Laboratories, "OPEN HOUSE 2016 'SHAPING the ATHLETIC BRAIN,'" [Online], 2016, NTT, [Retrieved on Sep. 25, 2018], Internet <URL:http://www.kecl.ntt.co.jp/openhouse/2016/exhibition/28/index.html>

Non-patent document 2: Hodges, P., and Bui, B. A comparison of computer-based methods for the determination of onset of muscle contraction using electromyography. Electroencephalogr. Clin. Neurophysiol. 101 (1996), 511-519.

SUMMARY OF THE INVENTION

Problem to be Solved by the Invention

When an athlete performs an exercise repeating repetitive movement such as cycling competition or running, an output of an electric potential may change in accordance with the changes in situation, such as conditions of the skin on which electrodes are provided and positions of the electrodes. A value of the electromyography acquired from the electrodes may change not by the movement of the muscle, but by the changes in the situation, such as sweating of an athlete or the position shift of the electrodes by the athlete performing an exercise for long hours.

However, in a method disclosed on Non-patent document 2, changes in noise caused by the athlete performing the exercise for long hours are not taken into consideration, and thus, it is not possible to acquire values of the electromyography appropriately removed with noise caused by changes in situations such as conditions of the skin and positions of the electrodes.

Accordingly, an object of the present invention is to provide an electromyography processing apparatus, an electromyography processing method, and an electromyography processing program of acquiring a value of an electromyography appropriately removed with noise during an athlete performs an exercise repeating repetitive movement.

Means for Solving the Problem

To solve the above problem, a first feature of the present invention relates to an electromyography processing apparatus that processes electromyography data indicating a time course of an electromyography acquired from an electrode set to a predetermined muscle of an athlete. The electromyography processing apparatus according to the first feature includes a storage device that stores the electromyography data of the predetermined muscle, a pre-processing unit that calculates a root-mean-square value in the electromyography data for each predetermined time and generates root-mean-square value data including the root-mean-square value for each time, and an onset detection unit that sets a sliding window for onset detection to a predetermined time of the root-mean-square value data and determines, if the average of the root-mean-square values in the sliding window is higher than a threshold value, that a predetermined time is an onset portion, and the onset detection unit further includes a threshold value determination unit that sets a sliding window for threshold value detection to a predetermined time and determines a threshold value based on the average of the root-mean-square values in a sliding window for threshold value detection. The sliding window for threshold value detection may be longer than a time of the sliding window for onset detection.

A second feature of the present invention relates to an electromyography processing apparatus that processes electromyography data indicating a time course of an electromyography acquired from an electrode set to a predetermined muscle of an athlete. The electromyography processing apparatus according to the second feature includes a storage device that stores the electromyography data of the predetermined muscle and an onset detection unit that determines that a portion is an onset portion based on an electromyography of the sliding window for onset detection and a threshold value, and the onset detection unit further includes a threshold value determination unit that determines a threshold value based on an electromyography of the sliding window for threshold value detection.

The sliding window for threshold value detection may be set in accordance with the sliding window for onset detection.

A third feature of the present invention relates to an electromyography processing method of processing electromyography data indicating a time course of an electromyography acquired from an electrode set to a predetermined muscle of an athlete. The electromyography processing method according to the third feature includes, storing, by a computer, the electromyography data of the predetermined muscle, calculating, by the computer, a root-mean-square value in the electromyography data for each predetermined time and generating root-mean-square value data including the root-mean-square value for each time, and setting, by the computer, a sliding window for onset detection to a predetermined time of the root-mean-square value data and determining, if the average of the root-mean-square values in the sliding window is higher than a threshold value, that a predetermined time is an onset portion, and the determining that the predetermined time is the onset portion includes setting a sliding window for threshold value detection to a predetermined time, and determining a threshold value based on the average of the root-mean-square values in the sliding window for threshold value detection.

A fourth feature of the present invention relates to an electromyography processing method of processing electromyography data indicating a time course of an electromyography acquired from an electrode set to a predetermined muscle of an athlete. The electromyography processing method according to the fourth feature includes storing, by a computer, the electromyography data of the predetermined muscle, and determining, by the computer, that a portion is an onset portion based on the electromyography of a sliding window for onset detection in the electromyography data and a threshold value, and the determining that the portion is the onset portion further includes determining a threshold value based on the electromyography of a sliding window for threshold value detection in the electromyography data.

A fifth feature of the present invention relates to an electromyography processing program for causing a computer to function as the electromyography processing apparatus described above.

EFFECT OF THE INVENTION

According to the present invention, it is possible to provide an electromyography processing apparatus, an electromyography processing method, and an electromyography processing program of acquiring a value of an electromyography appropriately removed with noise during an athlete performs an exercise repeating repetitive movement.

BRIEF DESCRIPTION OF THE DRAWINGS

FIG. 7 is an example of a signal input/output to/from a pre-processing unit according to an embodiment of the present invention.

FIG. 10 is a diagram illustrating a sliding window set by an onset detection unit according to an embodiment of the present invention and an onset section detected by the onset detection unit.

FIG. 13 is an example of a signal used when a dynamic threshold value is calculated by a threshold value determination unit according to an embodiment of the present invention.

FIG. 14 is an example of a smoothed ON/OFF indicator output by an ON/OFF indicator processing unit according to an embodiment of the present invention.

FIG. 15 is a flowchart illustrating ON/OFF indicator processes performed by an ON/OFF indicator processing unit according to an embodiment of the present invention.

FIG. 16 is an example of a signal used when an ON/OFF indicator is calculated by an ON/OFF indicator processing unit according to the embodiment of the present invention and illustrates a mathematical formula of a probability distribution used when the ON/OFF indicator is calculated.

FIG. 17 is a mathematical formula used when an ON/OFF indicator is calculated by an ON/OFF indicator processing unit according to an embodiment of the present invention.

FIG. 18 is an example of a probability distribution used when an ON/OFF indicator is calculated by an ON/OFF indicator processing unit according to an embodiment of the present invention.

FIG. 19 is an example of an RMS averaged value calculated by a balance indicator processing unit according to an embodiment of the present invention.

FIG. 20 is an example of a balance evaluation value calculated by a balance indicator processing unit according to an embodiment of the present invention.

MODE FOR CARRYING OUT THE INVENTION

Figure 1:
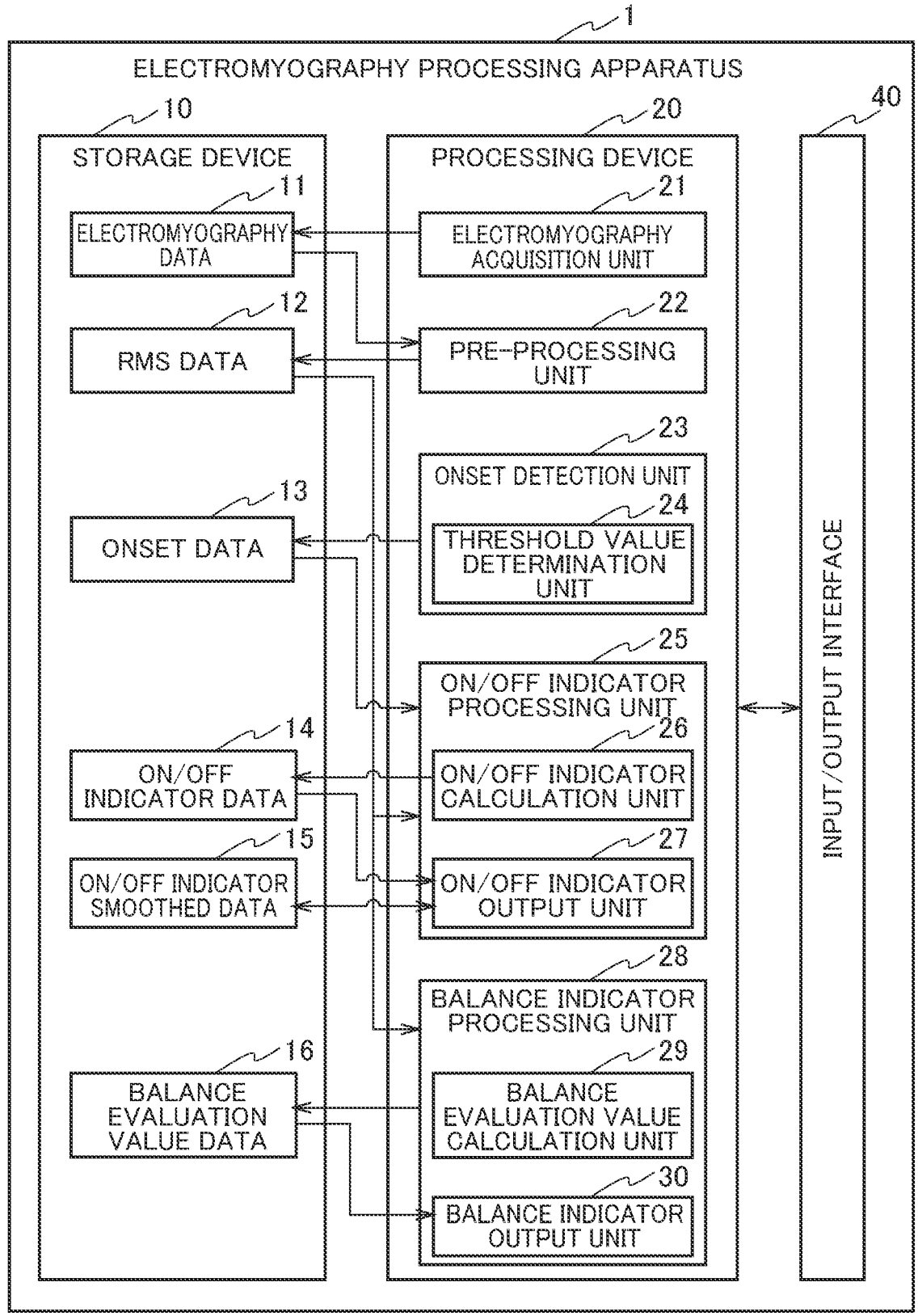
FIG. 1 is a diagram illustrating hardware and functional blocks of an electromyography processing apparatus according to an embodiment of the present invention.

Next, an embodiment of the present invention will be described with reference to the drawings. In the following illustration of the drawings, the same or similar parts are denoted with the same or similar reference numerals.

Electromyography Processing Apparatus

An electromyography processing apparatus 1 according to an embodiment of the present invention will be described with reference to FIG. 1. The electromyography processing apparatus 1 outputs data that enables an athlete who performs a repetitive exercise such as a cycling competition or running to recognize the change in a muscle movement during the repetitive exercise.

Figures 2, 3, 4:
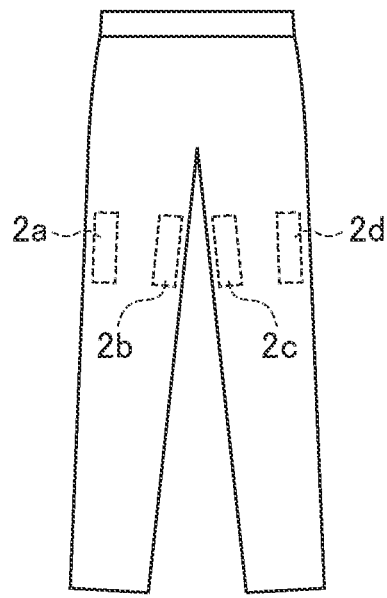
FIG. 2 is a diagram illustrating an example of tights provided with electrodes.
FIG. 3 is a diagram illustrating an example of a data structure of onset data according to an embodiment of the present invention.
FIG. 4 is a diagram illustrating an example of a data structure of ON/OFF indicator data according to an embodiment of the present invention.

As illustrated in FIG. 2, electrodes 2a to 2d are provided inside clothes worn by the athlete, and the electrodes 2a to 2d are in contact with the skin of the athlete. The electromyography processing apparatus 1 acquires an electromyography of a muscle located under a skin position corresponding to a position where the electrodes are provided with the electrodes 2a to 2d. The electrodes 2a to 2d may be attached to the skin of the athlete.

In an example illustrated in FIG. 2, the electrodes 2a and 2d acquire electromyographies of left and right vastus lateralis muscles, respectively. The electrodes 2a and 2b acquire electromyographies of left and right hamstrings, respectively. The electromyography processing apparatus 1 sequentially acquires the electromyographies acquired from the electrodes during an exercise by the athlete, analyzes the acquired electromyography, and outputs the analyzed electromyographies. If the electrodes 2a to 2d are not particularly distinguished, the electrodes 2a to 2d may be collectively referred to as electrodes 2. It should be noted that the positions to which the electrodes 2 are located and the number of the electrodes 2 illustrated in FIG. 2 are an example, and the present invention is not limited to the position and the number. The electrodes 2 are provided at positions at which an electromyography of an appropriately set muscle to be measured can be acquired.

The electromyography processing apparatus 1 is a general computer having a storage device 10, a processing device 20, and an input/output interface 40. By the general computer executing an electromyography processing program, functions illustrated in FIG. 1 are realized.

The storage device 10 is an ROM (Read-Only Memory), an RAM (Random-Access Memory), a hard disk, or the like, and stores various pieces of data such as input data, output data, and intermediate data which are for the processing device 20 to perform processes. The processing device 20 is a CPU (Central Processing Unit) which reads/writes from/to data stored in the storage device 10, inputs data and receives data via the input/output interface 40 to perform processes of the electromyography processing apparatus 1. The input/output interface 40 is an interface through which the electromyography processing apparatus 1 acquires electromyography data from the electrodes 2 and outputs the acquired electromyography data to a display device for outputting a processing result.

The storage device 10 stores the electromyography processing program, and also stores electromyography data 11, RMS data 12, onset data 13, ON/OFF indicator data 14, ON/OFF indicator smoothed data 15, and balance evaluation value data 16.

The electromyography data 11 is data indicating a time course of an electromyography acquired from the electrodes 2 set to a predetermined muscle of the athlete. The electromyography data 11 is data in which a value of the electromyography acquired from the electrodes 2 is associated with an acquired time. If electromyographies are acquired from a plurality of muscles, the electromyography data 11 is generated for each muscle.

The RMS data 12 includes a root-mean-square value (Root-mean-square value: RMS) of the electromyography for each predetermined time. The RMS data 12 is data in which a calculated root-mean-square value of the electromyography is associated with a time corresponding to the root-mean-square value. If the electromyography data 11 includes the electromyographies of the plurality of muscles, the RMS data 12 is generated for each muscle.

The onset data 13 specifies a section (an onset section) in which the electromyography increases in the electromyography data 11. The onset data 13 is, for example, as illustrated in FIG. 3, data in which an onset identifier for specifying the onset section is associated with a start time and an end time of the onset section. If the electromyography data 11 is generated for each of the plurality of muscles, the onset data 13 is generated for each muscle.

The ON/OFF indicator data 14 includes an ON/OFF indicator output by the ON/OFF indicator processing unit 25 which will be described later. The ON/OFF indicator is an indicator of a time required for an ON/OFF switching of the muscle in each ON/OFF section. The ON/OFF indicator data 14 is, for example, as illustrated in FIG. 4, data in which the ON/OFF indicator in the onset section is associated with the onset identifier for specifying the onset section. If the electromyography data 11 is generated for each of the plurality of muscles, the ON/OFF indicator data 14 is generated for each muscle.

The ON/OFF indicator smoothed data 15 includes an indicator acquired by smoothing the ON/OFF indicator of the ON/OFF indicator data 14. If the electromyography data 11 is generated for each of the plurality of muscles, the ON/OFF indicator smoothed data 15 is generated for each muscle.

Figures 5, 6:
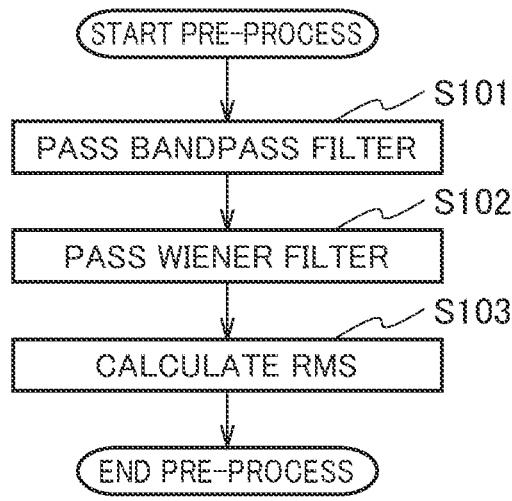
FIG. 5 is a diagram illustrating an example of a data structure of balance evaluation value data according to an embodiment of the present invention.
FIG. 6 is a flowchart explaining pre-processes performed by a pre-processing unit according to an embodiment of the present invention.

The balance evaluation value data 16 includes a balance evaluation value output by the balance indicator processing unit 28 which will be described later. The balance evaluation value is an evaluation value for comparing the amount of increase of each muscle used during the repetitive exercise. As illustrated in FIG. 5, for example, in the balance evaluation value data 16, a time, a muscle identifier for identifying a muscle, and a balance evaluation value calculated for the time and the muscle are associated with one another. In the balance evaluation value data 16, within a predetermined time, a plurality of combinations, each combination having a muscle identifier and a balance evaluation value, are associated.

The processing device 20 includes an electromyography acquisition unit 21, a pre-processing unit 22, an onset detection unit 23, an ON/OFF indicator processing unit 25, and a balance indicator processing unit 28.

Electromyography Acquisition Unit

The electromyography acquisition unit 21 acquires the electromyography acquired by the electrodes 2 and generates the electromyography data 11 in which the acquired electromyography is associated with a time at which the electromyography is acquired. If the electromyographies are acquired from the plurality of electrodes, the electromyography acquisition unit 21 generates the electromyography data 11 for each muscle corresponding to each of the electrodes.

Pre-processing Unit

The pre-processing unit 22 removes noise from the value of the electromyography in the electromyography data 11, calculates the root-mean-square value based on the value of the electromyography after noise removal, and generates the RMS data 12. The pre-processing unit 22 calculates the root-mean-square value in the electromyography data 11 for each predetermined time, and generates root-mean-square value data (RMS data 12) including the root-mean-square value for each time. If the electromyographies of the plurality of muscles are acquired, the pre-processing unit 22 generates the RMS data 12 for each muscle.

With reference to FIG. 6, pre-processes performed by the pre-processing unit 22 will be described.

First, in step S101, the pre-processing unit 22 passes a bandpass filter on the electromyography data 11. In step S102, the pre-processing unit 22 passes a Wiener filter on the data on which the bandpass filter has been passed in step S101. In step S103, the pre-processing unit 22 calculates the root-mean-square value of the data on which the Wiener filter has been passed in step S102 and generates the RMS data 12.

The pre-processing unit 22 passes the bandpass filter on the electromyography data 11 and filters frequencies other than frequencies of the electromyography. The electromyography data 11 with the electromyography acquired from the electrodes 2 includes various noises such as a noise caused by the movement of a body called "motion artifact" and a noise caused by the electricity generated on the skin, even if the athlete is not moving. The bandpass filter is passed on the electromyography data 11 so as to eliminate a noise other than a frequency band of the electromyography. Accordingly, frequencies of the electromyography data 11 can be narrowed down to the frequency band of the electromyography to be acquired.

A frequency of the bandpass filter is set in accordance with the noise included in the electromyography data 11. A filter used by the pre-processing unit 22 is not limited to the bandpass filter defining an upper limit value and a lower limit value, but may be a highpass filter or a lowpass filter that does not define either one of the upper limit value and the lower limit value. The upper and lower limit values of the bandpass filter are determined based on sampling frequencies of the acquired electromyography or characteristics of devices. For example, if the sampling frequency is 500 Hz, based on a sampling theorem, the upper limit value is set to be 249 Hz and the lower limit value is set to be 10 Hz from a main frequency characteristic of the electromyography. As how to filter frequencies, for example, a Butterworth filter is general, but the present invention is not limited to the method.

The pre-processing unit 22 applies the Wiener filter on the data on which the bandpass filter has been passed, removes noises on the entire electromyography data 11, and removes signals (noises) other than an electric signal generated by activating the muscle. If data acquired for measuring the intensity of the noise is present, the intensity of the noise removal of the Wiener filter is determined based on the data. Alternatively, if the intensity of the noise is not measured, the intensity of the noise removal is determined based on the electromyography data 11. The pre-processing unit 22 determines the intensity of the noise removal based on, for example, the electromyographies of the entire sections (each time) of the electromyography data 11. Alternatively, the pre-processing unit 22 may specify the onset section through processes that are the same as those performed by the onset detection unit 23 described later, based on the electromyography data 11 or the data on which the bandpass filter has been passed, and determine the intensity of the noise removal based on the electromyography of the non-onset section.

The pre-processing unit 22 applies the bandpass filter and the Wiener filter on the electromyography data 11 illustrated in FIG. 7(a) to remove the noise from the data, and accordingly, data illustrated in FIG. 7(b) can be acquired. When compared with the data illustrated in FIG. 7(a), in the data illustrated in FIG. 7(b), a section in which the voltage is close to 0 and a section in which the voltage is not 0 can be easily distinguished from each other.

Figure 8:
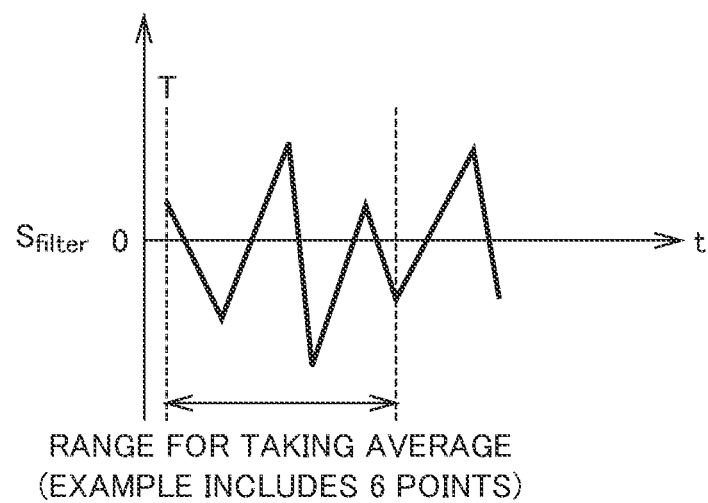
FIG. 8 is a diagram explaining a root-mean-square value calculated by a pre-processing unit according to an embodiment of the present invention.

Further, the pre-processing unit 22 calculates the root-mean-square value of the data on which the bandpass filter and the Wiener filter have been passed. As illustrated in FIG. 8(a), the pre-processing unit 22 calculates r(T), which is the root-mean-square value of data included in a range for taking the average within the data on which the filters have been passed, based on a formula illustrated in FIG. 8(b). The pre-processing unit 22 repeats the process of calculating the root-mean-square value for each section to generate the RMS data 12.

Accordingly, the pre-processing unit 22 can acquire data illustrated in FIG. 7(c). When compared with a signal illustrated in FIG. 7(b), in a signal illustrated in FIG. 7(c), the output of the electromyography in one motion can be expressed as one block.

Onset Detection Unit

The onset detection unit 23 detects an onset section in which the electromyography is increased by the repetitive exercise made by the athlete in the electromyography data 11. The onset detection unit 23 refers to the RMS data 12 subjected to the process of removing the noise from the electromyography data 11 or the like, specifies a section in a time direction in which the output of the electromyography is a predetermined threshold value or more as the onset section, and outputs the onset data 13. The onset detection unit 23 sets a sliding window for onset detection to a predetermined time of the RMS data 12, and if the average of the root-mean-square values in the sliding window is higher than the threshold value, the onset detection unit 23 determines that the predetermined time is an onset portion. The onset detection unit 23 specifies a section in which the onset portions continues as an onset section and outputs the onset data 13. The onset section detected by the onset detection unit 23 is processed by the ON/OFF indicator processing unit 25 which will be described later.

Figure 9:
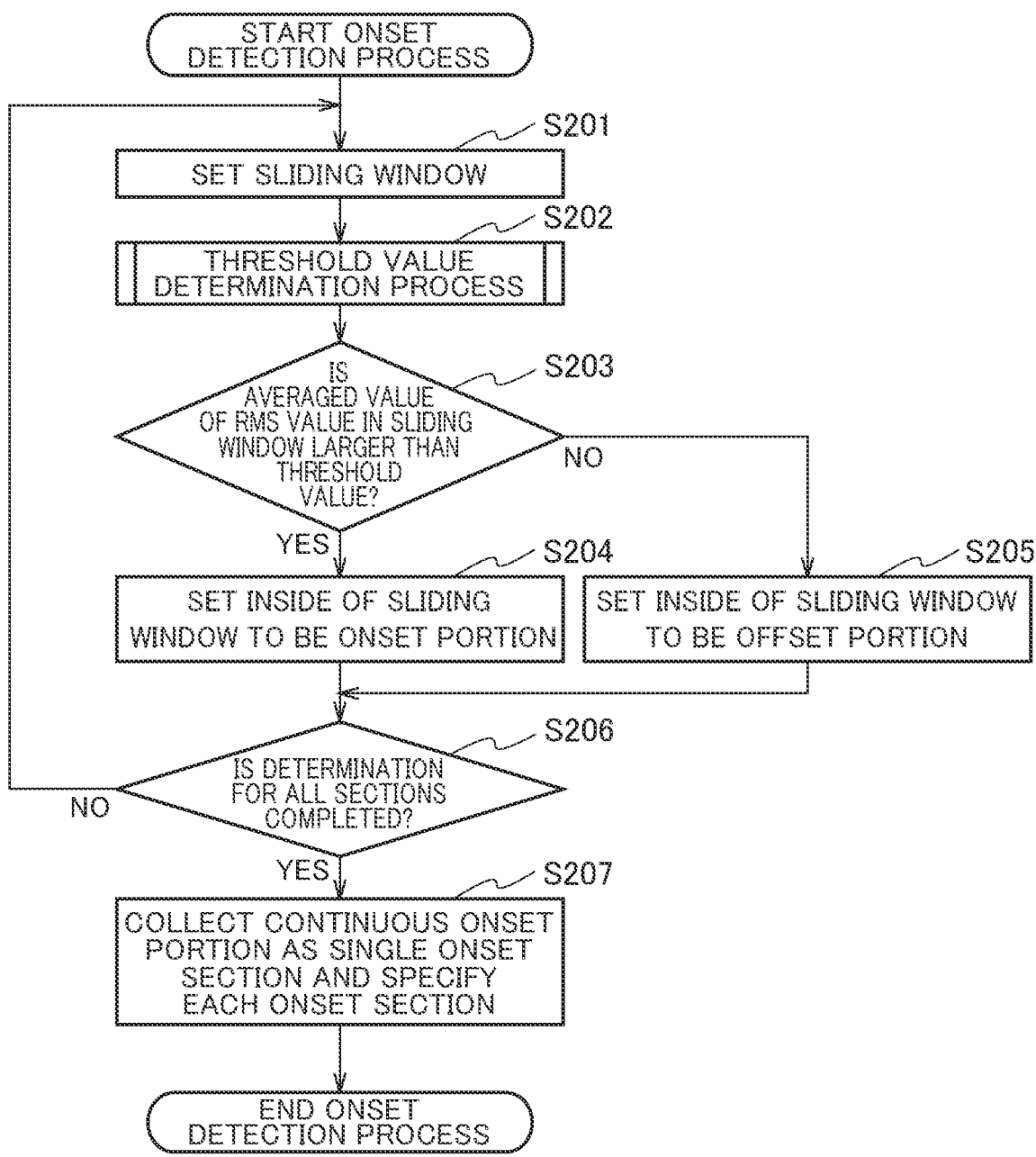
FIG. 9 is a flowchart explaining onset detection processes performed by an onset detection unit according to an embodiment of the present invention.

With reference to FIG. 9, onset detection processes performed by the onset detection unit 23 will be described.

In step S201, the onset detection unit 23 sets the sliding window that moves in the time direction. For example, as illustrated in FIG. 10(a), the sliding window for onset detection is set in the time direction. A time width of the sliding window for onset detection is $t_w$.

In step S202, a threshold value determination unit 24 in the onset detection unit 23 determines the threshold value for specifying the onset section. The process for determining the threshold value will be described later in detail with reference to FIG. 11.

In step S203, the onset detection unit 23 determines whether an averaged value of RMS values in the sliding window set in step S201 is more than the threshold value determined in step S202. If the averaged value is more than the threshold value, the onset detection unit 23 sets the inside of the sliding window to be the onset portion in step S204, and alternatively, if the averaged value is less than the threshold value, the onset detection unit 23 sets the inside of the sliding window to be an offset portion in step S205.

In step S206, the onset detection unit 23 determines whether the sliding window covers all times of the RMS data 12 and determines whether determination for all sections is completed. If the determination for all sections is not completed, the sliding window is moved in step S201, and processes of steps S202 to S205 are performed based on the moved sliding window. For example, as illustrated in FIG. 10(b), the sliding window is shifted by $t_{step}$ and a next sliding window is set. A time width of the next sliding window is $t_w$ as same as that of the sliding window for onset detection. For example, a window width of the sliding window for detecting onset section is 0.2 seconds, and a moving width is 0.1 seconds.

If the determination for all sections is completed, in step S207, the onset detection unit 23 collects the continuous onset portions as a single onset section and specifies each onset section. If the time detected as the onset portion in step S204 is continuous with the time detected as another onset portion, the onset detection unit 23 sets the continuous onset portions as a single onset section. As a result, as illustrated in FIG. 10(b), a plurality of onset sections can be specified among the measurement time of the repetitive exercise. The onset detection unit 23 specifies a start time and an end time of each onset section and generates the onset data 13.

The processes illustrated in FIG. 9 are an example, and the present invention is not limited to the processes. If the window width of the sliding window for detecting the onset section is 0.2 seconds and the moving width is 0.1 seconds, the determination as to whether the predetermined section is the onset section is repeated two times. In this case, if it is determined that the predetermined section is the onset section in either one of the two determinations, the predetermined section may be determined as the onset section. Alternatively, if the predetermined section is determined to be the onset section in both of the two determinations, the predetermined section may be determined as the onset section, and in other cases, the predetermined section may not be determined as the onset section. The same applies to a case where the determination as to whether the predetermined section is the onset section is repeated three or more times, and in this case also, the determination may be made based on a plurality of determination results in the predetermined section.

Threshold Value Determination Unit

The onset detection unit 23 includes the threshold value determination unit 24. The threshold value determination unit 24 determines a threshold value for detecting the onset section. The threshold value determined by the threshold value determination unit 24 is a static threshold value or a dynamic threshold value.

The static threshold value is a fixed value used for detecting the onset section in all sections of the measurement time of the repetitive exercise. When determining the static threshold value, the threshold value determination unit 24 determines the static threshold value based on the data of the electromyography measured in advance when the athlete is static by using a threshold-based method disclosed in Non-patent document 2. The static threshold value is applied at each time of the RMS data 12 and is suitable for a static environment such as a laboratory and a short time measurement.

The dynamic threshold value is a variable value calculated each time the onset section is determined. When determining the dynamic threshold value, the threshold value determination unit 24 sets a sliding window for threshold value detection with a time longer than a time of the sliding window for onset detection to a time of the detection of the onset, and determines the threshold value based on the average of the root-mean-square values in the sliding window for onset detection. A section for calculating the dynamic threshold value is specified corresponding to a section for calculating the ON/OFF indicator, and the dynamic threshold value is set. The threshold value can be determined depending on the noise of the electromyography measured through the electrodes 2 caused by the change in situations such as sweating of the athlete and the shifting of electrode positions during the repetitive exercise. This enables the determination of the noise in correspondence with the change in a measured value caused by the change in states of the skin and the electrodes, the change in a magnitude of a muscle output or the like due to the measurement during the repetitive exercise in the long term, and accordingly the noise can be appropriately removed.

Figure 11:
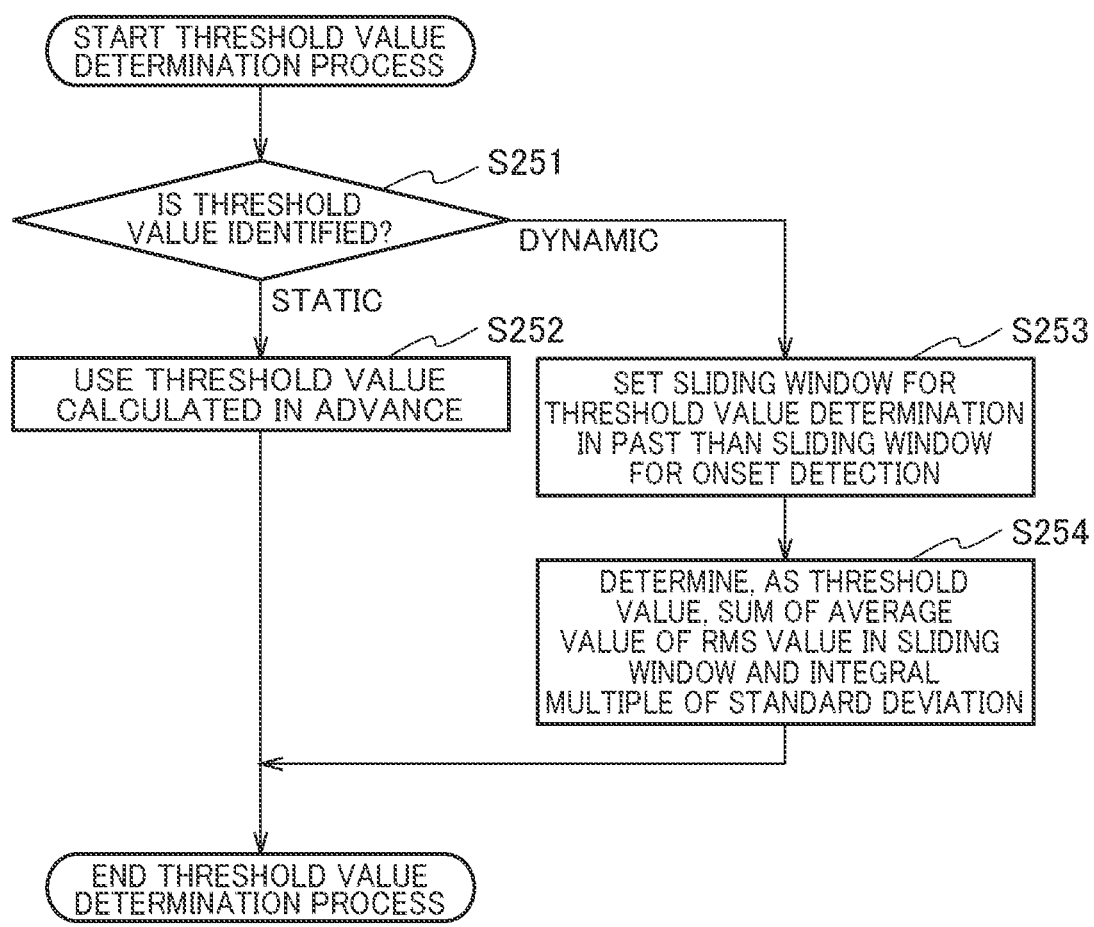
FIG. 11 is a flowchart explaining threshold value determination processes performed by a threshold value determination unit according to an embodiment of the present invention.

With reference to FIG. 11, threshold value determination processes performed by the threshold value determination unit 24 will be described.

First, in step S251, the static threshold value or the dynamic threshold value is selected as a threshold value type. If the static threshold value is selected, the threshold value determination unit 24 uses the static threshold value calculated in advance in step S252.

Alternatively, if the dynamic threshold value is selected, the threshold value determination unit 24 sets the sliding window for threshold value determination in the past than the sliding window for onset detection in step S253. In step S254, the threshold value determination unit 24 determines, as the threshold value, the sum of an average value of the RMS values in the sliding window for threshold value determination and the integral multiple of the standard deviation in the sliding window for threshold value determination.

In the embodiment of the present invention, a case where the threshold value type is selected each time the onset detection unit 23 sets the sliding window is described, but a predetermined threshold value type may be selected in advance.

Figure 12:
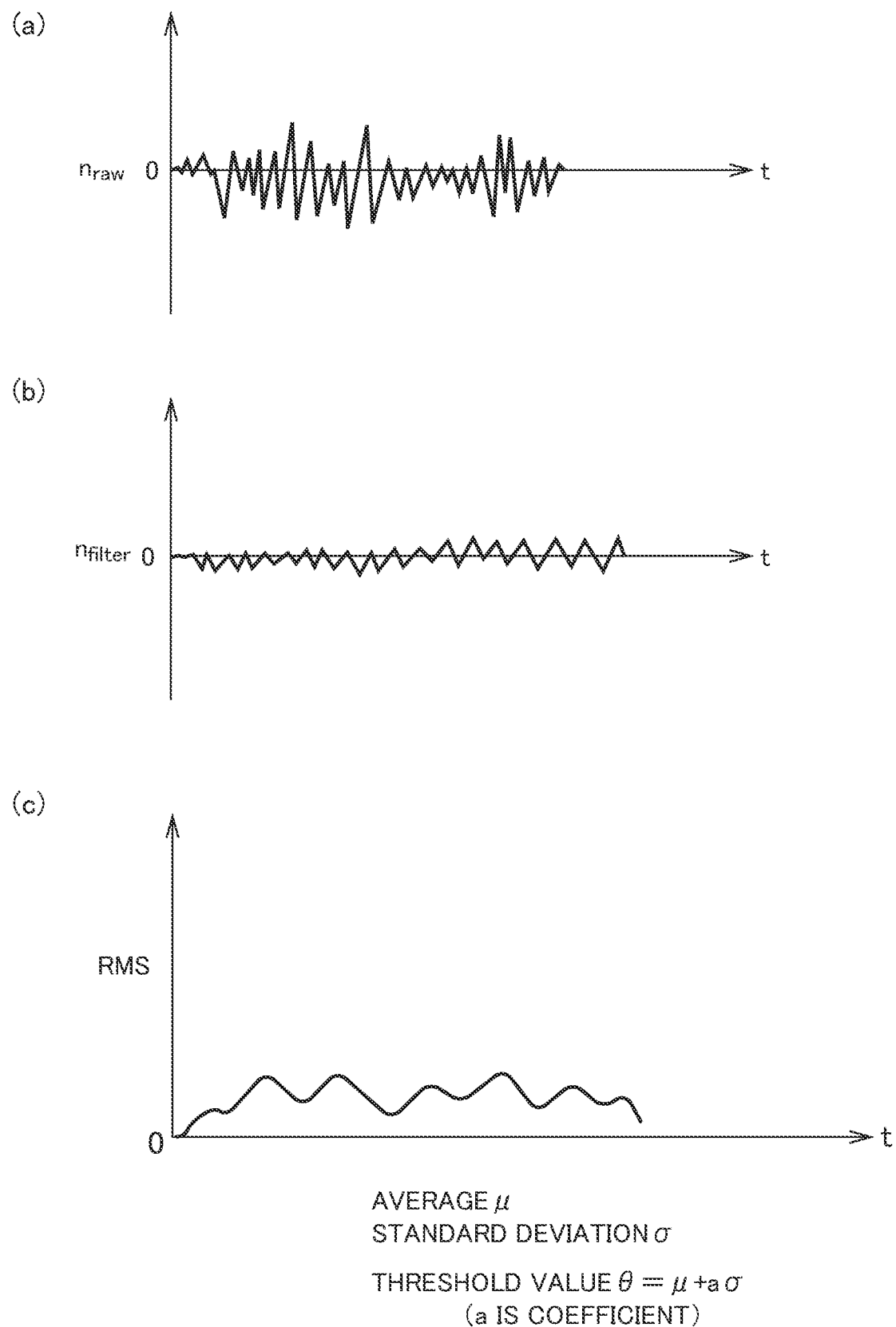
FIG. 12 is an example of a signal used when a static threshold value is calculated by a threshold value determination unit according to an embodiment of the present invention.

How to calculate the static threshold value will be described with reference to FIG. 12. The electrodes 2 are provided to the muscle to be measured in a state where a subject is doing nothing, and the transition of the electromyography is measured as illustrated in FIG. 12(a). Next, if the noise is removed from the measured electromyography through the same processes as those of the pre-processing unit 22, a signal illustrated in FIG. 12(b) is acquired. If the RMS value for the signal illustrated in FIG. 12(b) is calculated, a signal indicating the transition of the RMS values as illustrated in FIG. 12(c) is acquired. The threshold value determination unit 24 determines, as a threshold value, a value acquired by adding the integral multiple of the standard deviation to the average value of the RMS values illustrated in FIG. 12(c).

In the embodiment of the present invention, a case where a value acquired by adding the integral multiple of the standard deviation to the average value of the RMS values is determined as the threshold value has been described, but the present invention is not limited to this cause. It is enough if the threshold value is determined based on the averaged value of the RMS values, and the threshold value may be determined based on other methods such as a method of determining, as the threshold value, a value acquired by adding a predetermined rate of a value of the averaged value of the RMS values to the averaged value of the RMS values.

How to calculate the dynamic threshold value will be described with reference to FIG. 13. As illustrated in FIG. 13(a), the width of the sliding window for threshold value detection is set to be two, and the width of the sliding window for onset detection is set to be $t_w$. The width $t_{w\theta}$ of the sliding window for threshold value detection is wider than the width $t_w$ of the sliding window for onset detection.

A sliding window WT1 for determining the threshold value is provided before a sliding window W1 to determine whether the sliding window W1 is the onset section. The threshold value determination unit 24 determines, as a threshold value $\theta_1$, the sum of an average value $\mu_1$ of the RMS values in the sliding window for threshold value determination WT1 and an integral multiple of a standard deviation $\sigma_1$ in the sliding window for threshold value determination WT1. The threshold value $\theta_1$ is used to determine whether the sliding window W1 for onset detection is the onset detection.

In a sliding window WT2 delayed from the sliding window WT1 for threshold value detection also, a threshold value is determined as in the sliding window WT1. A threshold value $\theta_2$ calculated in the sliding window WT2 for threshold value detection is used to determine whether the sliding window WT2 for onset detection is the onset section.

The dynamic threshold value is calculated by providing the sliding window for threshold value detection in correspondence with the sliding window for onset detection, and thus, as illustrated in FIG. 13(b), the threshold value $\theta$ dynamically changes according to the time. Therefore, even if situation changes are caused such as sweating of the athlete, the shifting of electrode positions, or the change in an external environment during the repetitive exercise, the threshold value determination unit 24 can set the threshold value by taking into consideration of the situation changes. Thus, the onset detection unit 23 can appropriately detect the onset section.

Further, in the embodiment of the present invention, the time of the sliding window WT1 for threshold value detection is set before the time of the sliding window W1 for onset detection, and thus, the sliding window WT1 for threshold value detection is suitable for making feedbacks while performing the measurement. Further, the sliding window for threshold value detection may be moved in correspondence with the sliding window for onset detection and may be set to be longer than the sliding window for onset detection, and the a position of the sliding window for threshold value detection relative to the sliding window for onset detection may be appropriately changed. For example, the sliding window for threshold value detection may be set to include the time of the sliding window for onset detection, or alternatively may be provided immediately after the sliding window for onset detection.

ON/OFF Indicator Processing Unit

The ON/OFF indicator processing unit 25 calculates an ON/OFF indicator of a time required for the ON/OFF switching of the muscle in each onset section detected by the onset detection unit 23. The ON/OFF indicator processing unit 25 includes an ON/OFF indicator calculation unit 26 and an ON/OFF indicator output unit 27.

The ON/OFF indicator calculation unit 26 calculates a variance of a probability distribution acquired by normalizing the root-mean-square value of the electromyography for each onset section, and outputs the calculated variance as an ON/OFF indicator for each onset section. The ON/OFF indicator calculation unit 26 outputs ON/OFF indicator data 14 in which the onset section is associated with the ON/OFF indicator of the onset section.

The ON/OFF indicator output unit 27 smooths a plurality of ON/OFF indicators of the onset section and outputs a time course of the smoothed ON/OFF indicator. The ON/OFF indicator output unit 27 outputs ON/OFF indicator smoothed data 15 with the smoothed ON/OFF indicator. Further the ON/OFF indicator output unit 27 outputs a time at which the smoothed ON/OFF indicator is higher than a predetermined threshold value, as a time at which the ON/OFF switching of the muscle is inappropriate.

The ON/OFF indicator processing unit 25 performs, to each RMS value of a predetermined onset section, a process to be regarded as the probability distribution in which a time is a random variable and the intensity is expressed with a probability density function, and repeats the process for regarding each onset section as the probability distribution. Specifically, in order to set a minimum value to be 0 in the predetermined onset section, after the minimum value is subtracted from each RSM value of the onset section, the normalization (a transformation in which the integral of the whole is equal to one) is performed in the onset section. Then, the variance in the probability distribution is calculated as the ON/OFF indicator in the predetermined onset section. Further, the ON/OFF indicator processing unit 25 repeats the process of calculating the ON/OFF indicator for each onset section.

A feature that the ON/OFF indicator is small means that the probability distribution that is the output of the electromyography is sharp. If the above is replaced with a phenomenon of a muscle movement, the feature means that the switching from an OFF state to an ON state, and alternatively, the switching from an ON state to an OFF state of each muscle are made quickly.

On the other hand, when the ON/OFF indicator is large, the probability distribution is spread as a whole, and this means that times and wastes are caused in the ON/OFF switching. In a case of an athlete who is not able to perform the ON/OFF switching well, actually, during a single motion, the graph is not unimodal, but two or three bumps may occur in the graph, and the ON/OFF indicator becomes large.

The ON/OFF indicator calculated by the ON/OFF indicator calculation unit 26 for each onset section varies greatly, and even if the ON/OFF indicator is graphed, the entire tendency is not easily viewed, and thus, the visibility is lacked. Therefore, the ON/OFF indicator output unit 27 can make the tendency clear by smoothing the ON/OFF indicator for each onset section, such as, for example, graphing the average of the ON/OFF indicators in the sliding window having a width of 60 seconds.

With reference to FIG. 14, an example of the smoothed ON/OFF indicator output by the ON/OFF indicator processing unit 25 is described. FIGS. 14(a) to 14(d) illustrate the transition of the smoothed ON/OFF indicator for the electromyographies of the left and right vastus lateralis muscles and the left and right hamstrings measured when four different subjects each pedals a bicycle for a long hours while increasing a load of a bicycle for each human subject every 2 minutes. Further, in each of the graphs illustrated in FIG. 14, if the smoothed ON/OFF indicator exceeds 3000, the subject becomes an improvement target.

It can be seen from the graphs that the ON/OFF switching of each muscle of each subject illustrated in FIG. 14(a) and FIG. 14(b) is made quickly, and it is observed that the muscles are effectively used.

With respect to a subject of FIG. 14(c), it can be observed that, from around 300 seconds, the left hamstring exceeds the threshold value of 3000, and the left hamstring is strained. With respect a subject illustrated in FIG. 14(d), the indicators for the left and right hamstrings become larger than the indicators for the left and right vastus lateralis muscles, and thus, it can be observed that a bias is caused in an agility of the ON/OFF switching of the muscles. It can be observed also that the subject illustrated in FIG. 14(d) has the low agility of the ON/OFF switching of each muscle.

In this way, by observing the time course of the ON/OFF indicator, it is possible to specify deteriorated parts of the indicator and to isolate a countermeasure method.

With reference to FIG. 15, the ON/OFF indicator processes performed by the ON/OFF indicator processing unit 25 will be described.

First, the ON/OFF indicator processing unit 25 repeats processes from steps S301 to S303 for each onset section and calculates the ON/OFF indicator for each onset section.

In step S301, the ON/OFF indicator processing unit 25 subtracts the minimum value of the RMS value of the onset section to be processed from each RMS value of the onset section to be processed, and shifts each RMS value such that the minimum value of the onset section to be processed becomes 0. In step S302, the ON/OFF indicator processing unit 25 normalizes a value acquired by performing the process of step S301. In step S303, the ON/OFF indicator processing unit 25 calculates the variance of the probability distribution acquired by the normalization made in step S302 as the ON/OFF indicator of the onset section to be processed. The ON/OFF indicator processing unit 25 generates the ON/OFF indicator data 14 based on the ON/OFF indicator for each onset section.

After the ON/OFF indicator is calculated for each onset section, the ON/OFF indicator processing unit 25 smooths the ON/OFF indicator in step S304 to generate the ON/OFF indicator smoothed data 15. Further, the ON/OFF indicator processing unit 25 outputs the smoothed ON/OFF indicator by using a graph or the like.

With reference to FIGS. 16 and 17, the ON/OFF indicator calculated by the ON/OFF indicator calculation unit 26 will be described.

FIG. 16(a) is a diagram in which the RMS data 12 is overlaid with each onset section of the onset data 13. Each onset section illustrated in FIG. 16(a) has different time widths and RMS values, and thus, to evaluate the time widths and the RMS values equally, the RMS values of each onset section are normalized by using a formula illustrated in FIG. 16(b), and then, the probability distribution P(t) is calculated. The probability distribution P(t) of a certain onset section is shown, for example, as in FIG. 16(c). An ON/OFF indicator at a time $t_e^{(1)}$ is calculated by the variance of the probability distribution P(t) as shown in a formula illustrated in FIG. 17.

For example, the probability distribution P(t) when the ON/OFF indicator is small has a sharp peak as illustrated in FIG. 18(a). On the other hand, the probability distribution P(t) when the ON/OFF indicator is large may be, for example, a distribution with a plurality of peaks as illustrated in FIG. 18(b), or may be a distribution with gentle peaks as illustrated in FIG. 18(c).

The ON/OFF indicators are smoothed to prevent the abrupt change in the ON/OFF indicators. For example, the average of variance values included in each range defined with $[0, t_w]$, $[t_{step}, t_w+t_{step}]$, $[2t_{step}, t_w+2t_{step}]$ . . . and the like may be output as the smoothed ON/OFF indicator of each range. By such calculation, the graphs illustrated in FIG. 14 are output. According to the graphs illustrated in FIG. 14, the tendency of the ON/OFF indicators during the exercise time can be confirmed.

Balance Indicator Processing Device

The balance indicator processing unit 28 calculates a balance evaluation value for comparing the amount of increase of each of the muscles used during the repetitive exercise based on the electromyography of each of the muscles acquired by the electromyography acquisition unit 21. Further, the balance indicator processing unit 28 compares the balance evaluation value of each of the muscles at a certain point of time, and outputs a balance indicator indicating the bias of the amount of increase of each of the muscles at that point of time. The balance indicator processing unit 28 includes a balance evaluation value calculation unit 29 and a balance indicator output unit 30.

The balance evaluation value calculation unit 29 calculates the root-mean-square value of the electromyography for each predetermined time, and outputs a value acquired by subjecting, to time differentiation, the time course of the averaged value of the root-mean-square value in the sliding window for calculating balance evaluation value as the balance evaluation value of the predetermined muscle. The balance evaluation value is the transition of the value acquired by subjecting, to time differentiation, the average value of the root-mean-square value. Further, the balance evaluation value calculation unit 29 repeats the process of calculating the balance evaluation value for each piece of electromyography data of each of the plurality of muscles, and outputs the balance evaluation value for each of the plurality of muscles.

The balance indicator output unit 30 outputs the balance indicator based on the balance evaluation value of each of the plurality of muscles. If the difference between a maximum value and a minimum value among the balance evaluation values of individual muscles at a predetermined time is large, the balance indicator output unit 30 outputs a balance indicator indicating that the balance of the muscles is inappropriate at the predetermined time. The balance indicator output unit 30 outputs a balance indicator indicating that a muscle having a balance evaluation value that is smaller than balance evaluation values of other muscles does not move appropriately based on the balance evaluation value of each of the muscles at the predetermined time.

The balance indicator processing unit 28 makes a conversion to a graph capable of comparing a temporal change in the electromyography of each of the muscles during measurement based on the RMS value. The balance indicator processing unit 28 calculates a time differentiation for the converted graph and converts the time differentiation into a balance evaluation value indicating the amount of increase of the output of each of the muscles. The balance evaluation value is a value for comparing each of the muscles with other muscles. The balance indicator processing unit 28 calculates the balance evaluation value for each muscle and outputs the balance indicator in which the balance evaluation value of each of the muscles is compared.

The balance indicator processing unit 28 outputs the balance indicator based on the difference among the balance evaluation value of each of the muscles at the same clock time. For example, if a user desires to observe only whether the dependency is made on a particular muscle, the balance indicator processing unit 28 calculates the difference between the maximum value and the minimum value among the balance evaluation value of each of the muscles at the same clock time. If the balance evaluation value is more than a predetermined value, the balance indicator processing unit 28 outputs a balance indicator indicating that the balance of the muscle at this point of time is inappropriate.

A feature that the difference between the maximum value and the minimum values of the balance indicators of each of the muscles at the same clock time is small means that the output of each of the muscles changes similarly. On the other hand, a feature that the difference between the maximum value and the minimum value of the balance indicator of each of the muscles at the same clock time is large means that how output changes largely varies for each of the muscles.

If a muscle applied with the dependency is to be specified, for example, if it is checked whether an operation depends on a vastus lateralis muscle, the balance indicator processing unit 28 calculates the difference between a balance evaluation value of the muscle and a balance evaluation value of the other muscle. If the balance evaluation value of the vastus lateralis muscle is lower than the balance evaluation value of the other muscle, the balance indicator processing unit 28 outputs a balance indicator indicating that the vastus lateralis muscle is not appropriately used.

Note that, it is meaningless to compare the output itself of the electromyography. The output of the electromyography varies depending not only on the output from the muscle, but also on positions where the electrodes 2 are mounted, and conditions of the muscles and the skin, and thus, the size itself of the electromyographies at a plurality of points may not be compared. Therefore, in the embodiment of the present invention, the balance indicator processing unit 28 evaluates the balance of each of the muscles based on the amount of increase of each of the muscles.

With reference to FIGS. 19 and 20, an example of a balance evaluation value calculated by the balance indicator processing unit 28 will be described. The (a) to (d) of FIGS. 19 and 20 respectively illustrate transitions of an RMS averaged value and the balance evaluation value for the electromyographies of the left and right vastus lateralis muscles and the left and right hamstrings measured when different subjects pedaled a bicycle for a long hours while raising a load of the bicycle every 2 minutes. FIGS. 19(*a*) and 20(*a*) illustrate pieces of data from the same subject, and the same applies to (b) to (d) of FIGS. 19 and 20.

With respect to a subject illustrated in (a) of each of FIGS. 19 and 20, the RMS averaged value of each of the muscles increases in the same way as illustrated in FIG. 19(*a*), and the balance evaluation value illustrated in FIG. 20(*a*) does not change in all sections. Further, with respect to a subject illustrated in (b) of each of FIGS. 19 and 20, the RMS averaged value of each of the muscles increases in the same way as illustrated in FIG. 19(*b*), and a time differentiation value illustrated in FIG. 20(*b*) does not change in all sections. Therefore, with respect to the respective subjects illustrated in (a) and (b) of each of FIGS. 19 and 20, it is considered that there is no difference in the balance evaluation value in each section and the subjects use each of the muscles appropriately.

On the other hand, with respect to a subject illustrated in (c) of each of FIGS. 19 and 20, as illustrated in FIG. 20(*c*), while the balance evaluation values of the left and right vastus lateralis muscles are becoming high from around 300 seconds, the balance evaluation values of the left and right hamstrings are low, and thus, the pedaling depends on some muscles.

On the other hand, with respect to a subject illustrated in (d) of each of FIGS. 19 and 20, while the balance evaluation values of the left and right vastus lateralis muscles are high is all sections, the balance evaluation values of the left and right hamstrings are low. Therefore, it can be considered that the subject illustrated in (d) of each of FIGS. 19 and 20 have not been able to intentionally use the hamstrings.

Figure 21:
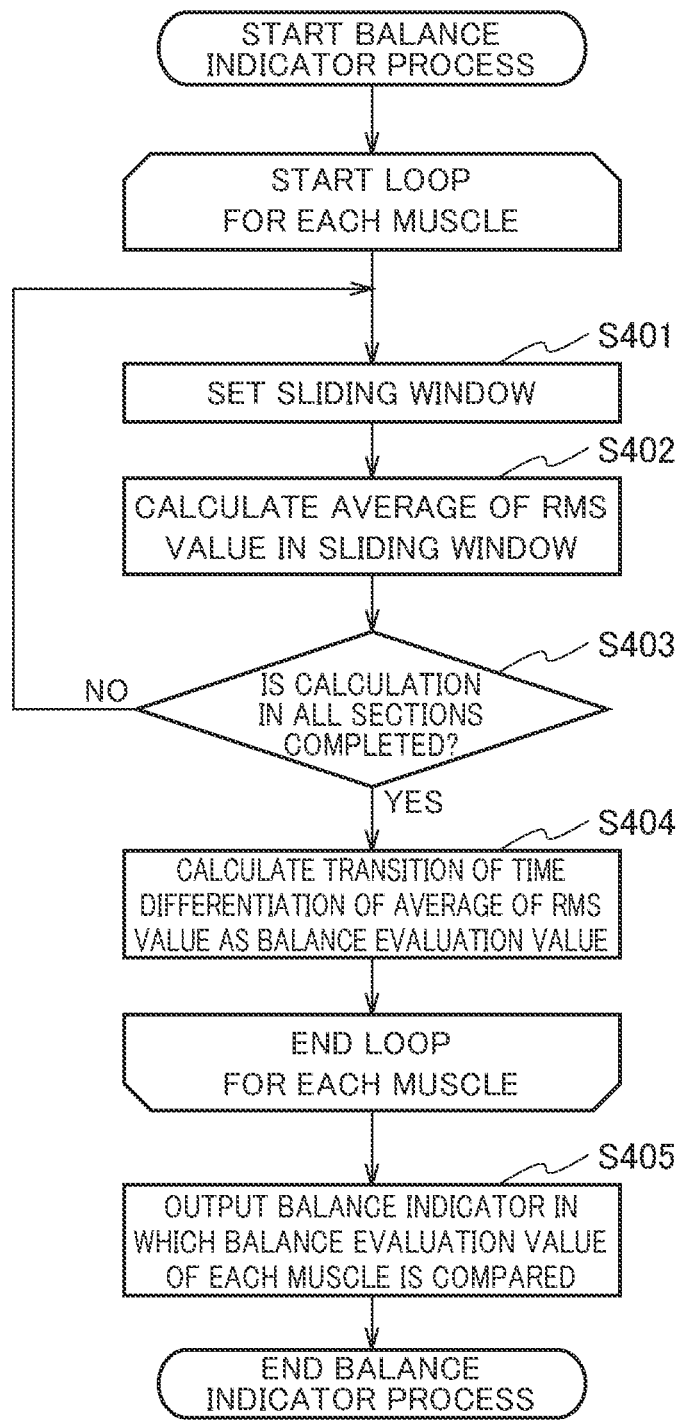
FIG. 21 is a flowchart explaining balance indicator processes performed by a balance indicator processing unit according to an embodiment of the present invention.

With reference to FIG. 21, balance indicator processes performed by the balance indicator processing unit 28 will be described.

First, the balance indicator processing unit 28 repeats processes from steps S401 to S404 for each muscle and calculates the transition of the balance evaluation value of each of the muscles.

Figure 22:
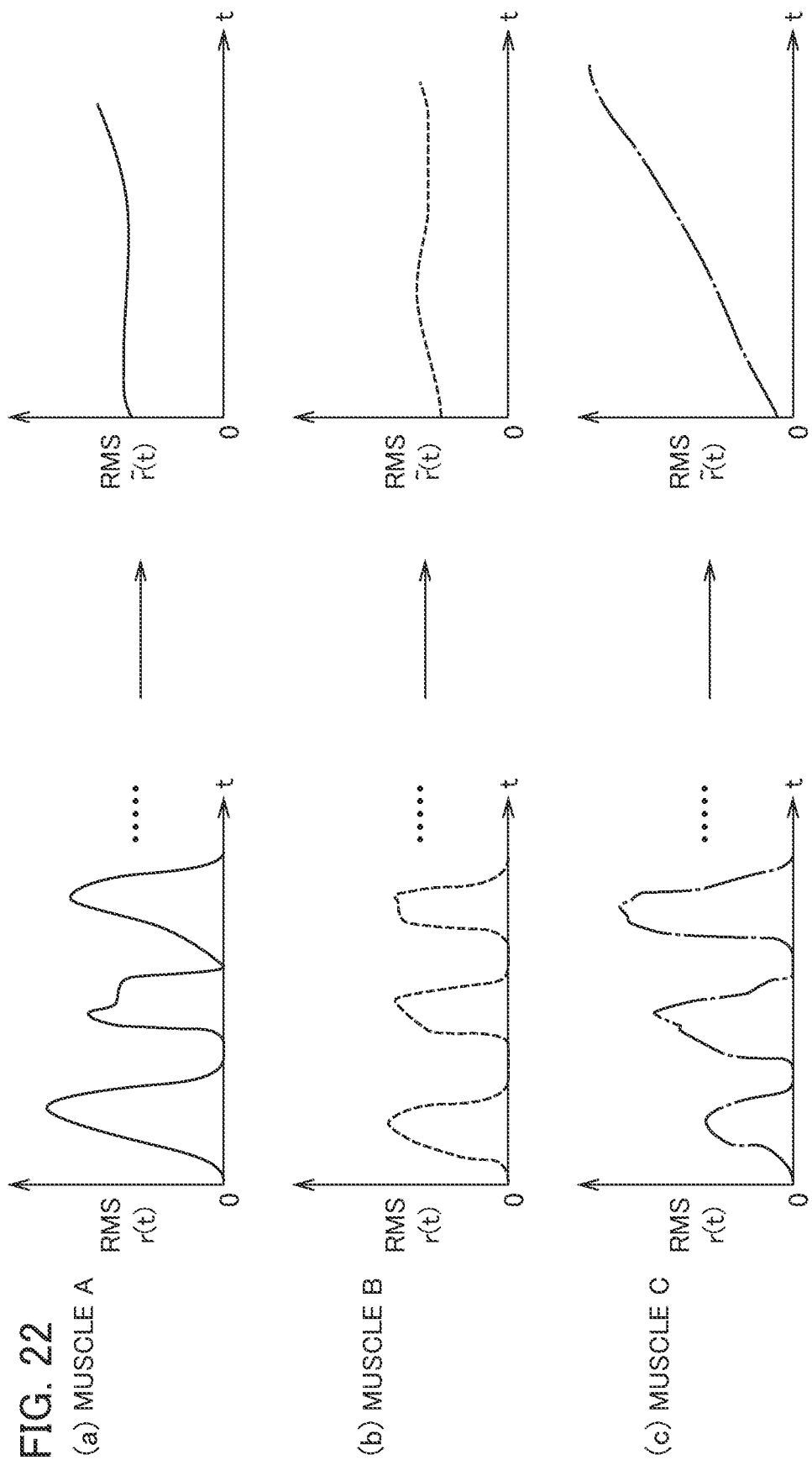
FIG. 22 is an example of pieces of data on an RMS value of each of the muscles and the averages of RMS values calculated by a balance indicator processing unit according to an embodiment of the present invention.

In step S401, the balance indicator processing unit 28 sets a sliding window of, for example, 60 seconds to the RMS data 12 and in step S402, takes the averages of the RMS values in the sliding window. In step S403, the balance indicator processing unit 28 calculates the average of the RMS values in all measurement sections while moving the sliding window. FIG. 22 illustrates an example in which the balance evaluation values are calculated from the RMS values for each of a muscle A, a muscle B, and a muscle C. In FIG. 22, the left side of two graphs of each of the muscle A, the muscle B and the muscle C shows the RMS values calculated with the sliding window of 0.1 seconds, and the right side shows the average of the RMS values calculated with the sliding window of 60 seconds.

Figure 23:
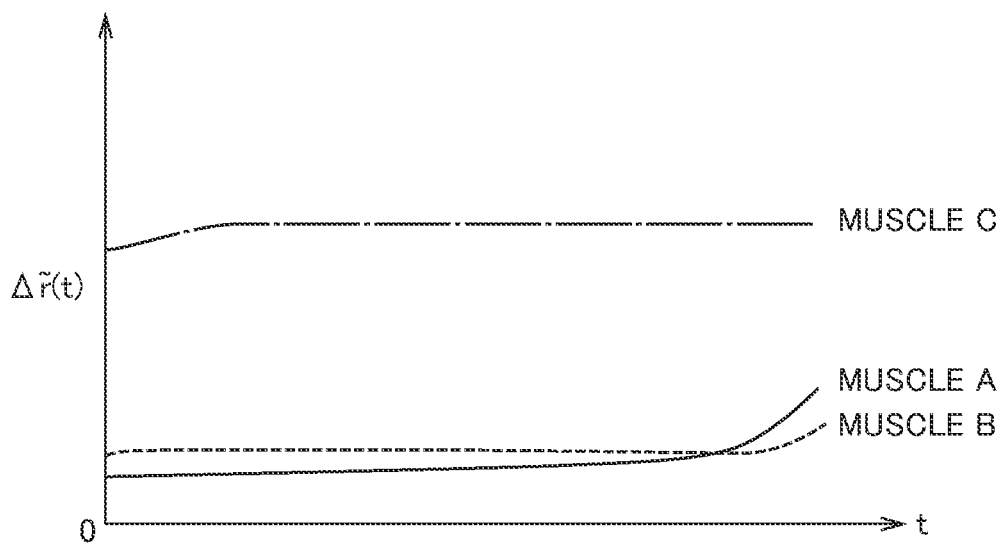
FIG. 23 is an example of a balance evaluation value calculated by a balance indicator processing unit according to an embodiment of the present invention.
Figure 24:
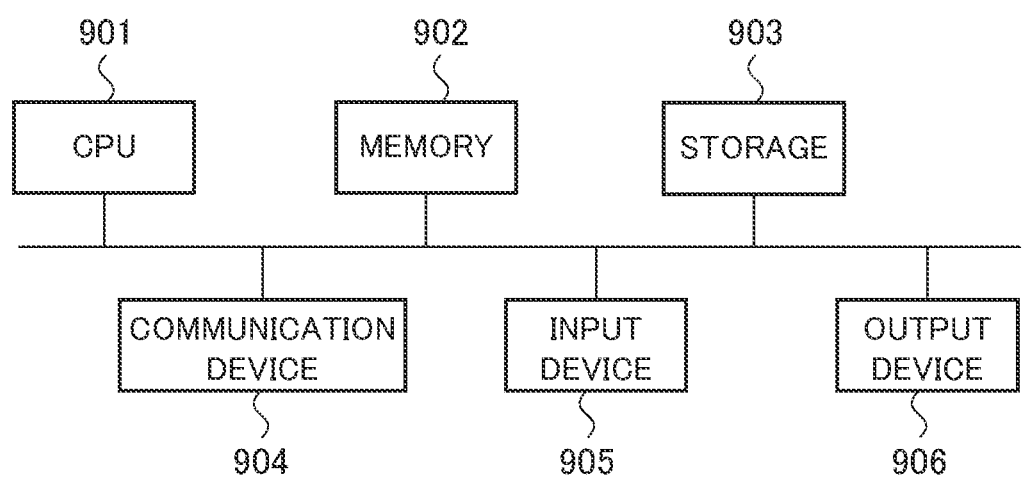
FIG. 24 is a diagram illustrating a hardware constitution of an electromyography processing apparatus.

After calculating the averaged value of the RMS values for all sections, in step S404, the balance indicator processing unit 28 calculates the transition of the time differentiation of the average of the RMS values as the balance evaluation value. FIG. 23 illustrates the transition of the balance evaluation values of the muscles A, B and C.

After calculating the balance evaluation value for each muscle, in step S405, the balance indicator processing unit 28 outputs a balance indicator in which balance evaluation value of each of the muscles is compared. As illustrated in FIG. 23, in all measurement sections, the balance evaluation value of the muscle C is larger than the balance evaluation values of the muscle A and the muscle B, and thus, it is considered that the difference between the maximum value and the minimum value of the balance indicator at each point of time is large. Accordingly, in the examples illustrated in FIG. 22 and FIG. 23, the balance indicator processing unit outputs a balance indicator indicating that a user performs an exercise by depending on a specific muscle in all measurement sections. The balance indicator of the muscle C is larger than the balance indicators of the muscle A and the muscle B, and thus, the balance indicator processing unit 28 recognizes that the user performs the exercise by depending on the muscle C.

In this way, the electromyography processing apparatus 1 according to the embodiment of the present invention can analyze the changes in the electromyography during the repetitive exercise.

The electromyography processing apparatus 1 can quantitatively indicate an ON/OFF switching speed in the muscle or an output size of each of the muscles by the ON/OFF indicator or the balance indicator.

Conventionally, in an endurance sport training, a load is determined based on an indicator of a heart rate and an indicator of power, and the training is performed for the purpose of improving the endurance capacity of each athlete. By referring to indicators calculated by the electromyography processing apparatus 1 according to the embodiment of the present invention, and by performing a training that can keep the indicator indicating a skill element for each purpose, the athlete himself/herself comes to be able to perform a training that is quantitative and is based on a theory for acquiring an efficient operation. Further, in the course of the training, it is possible to advance the training while quantitatively confirming the degree of progress for each element.

The electromyography processing apparatus 1 according to the embodiment of the present invention can sequentially measure the electromyography while the athlete repeats the repetitive exercise for a long hours, and can output an ON/OFF indicator that quantitatively indexes a time required for the ON/OFF switching of the muscle, from the change in the electromyography. This can quantify the agility of the the ON/OFF switching of the muscle during the athlete performs the exercise repeating repetitive movement.

The electromyography processing apparatus 1 can sequentially measure the electromyography while the athlete repeats the repetitive exercise for a long hours, and can output a balance indicator indexing whether each of the muscles is moving in a well-balanced manner, such as the strain of only a predetermined muscle, from the change in the electromyography. This can quantify whether the dependency is made on the predetermined muscle during the athlete performs the exercise repeating repetitive movement.

If the electromyography is sequentially measured while the repetitive exercise is repeated for long hours, a threshold value for specifying the onset section can be determined by taking into consideration of noises caused in response to changes in situations, such as shifting of the electrodes 2 and a change in a state of the skin. This enables the acquisition of a value of the electromyography appropriately removed with the noises during the athlete performs the exercise repeating repetitive movement.

Another Embodiment of the Onset Detection Unit

The onset detection unit 23 determines the onset portion based on the electromyography of the sliding window for onset detection and a threshold value.

More specifically, the pre-processing unit 22 calculates the root-mean-square value of the electromyography data 11 for each predetermined time, and generates the root-mean-square value data (the RMS data) 12 including the root-mean-square value for each time. The onset detection unit 23 sets the sliding window for onset detection to the predetermined time of the RMS data 12 and, if the average of the root-mean-square values (RMS values) in the sliding window is higher than a threshold value, the onset detection unit 23 determines that the predetermined time is the onset portion. The predetermined time is a time for determining whether the predetermined time is an onset portion.

The threshold value determination unit 24 determines a threshold value based on the electromyography of the sliding window for threshold value detection. Whether the time in the sliding window for onset detection is the onset portion is determined based on the threshold value calculated from the electromyography in the sliding window for threshold value detection.

More specifically, the threshold value determination unit 24 sets the sliding window for threshold value detection to the predetermined time, and determines a threshold value based on the average of the root-mean-square values in the sliding window for threshold value detection.

The sliding window for threshold value detection is set in accordance with the sliding window for onset detection.

The sliding window for threshold value detection is longer than a time of the sliding window for onset detection.

In correspondence with the movement of the sliding window for onset detection, the sliding window for threshold value detection is moves also.

Each time the sliding window for onset detection moves, the sliding window for threshold value detection may move. Alternatively, the frequency of the movement of the sliding window for threshold value detection may be lower than the frequency of the movement of the sliding window for onset detection. When the onset is detected, the threshold value that is calculated most recently may be used.

The value of the electromyographies acquired from the electrodes may change not by the movement of the muscle but by the changes in the situation, such as sweating of the athlete or the position shift of the electrodes by the athlete performing the exercise for long hours. The onset detection unit 23 uses a threshold value dynamically calculated from the electromyography of the sliding window for threshold value detection instead of using a fixed threshold value, and therefore, it is possible to determine a threshold value in accordance with an exercise status.

Another Embodiment of ON/OFF Indicator Processing Unit

The ON/OFF indicator output by the ON/OFF indicator processing unit 25 indicates a time required for switching between the onset section and an offset section. The offset section is a section other than the onset section.

The ON/OFF indicator processing unit 25 calculates the ON/OFF indicator from the variation of the electromyography in each onset section.

The variation of the electromyography is calculated by the variance in which the electromyography in the onset section is viewed as the probability distribution. More specifically, the ON/OFF indicator processing unit 25 calculates the variance of the probability distribution acquired by normalizing the root-mean-square value of the electromyography for each onset section detected by the onset detection unit 23, and outputs the calculated variance as the ON/OFF indicator for each onset section.

The ON/OFF indicator processing unit 25 outputs the ON/OFF indicator for each muscle and for each onset section. The ON/OFF indicator processing unit 25 may output the transition of the ON/OFF indicator for each muscle.

A small ON/OFF indicator means that the variation of the electromyography in the onset section is small. The small ON/OFF indicator indicates that the output of the electromyography is steep and the electromyography becomes high only when necessary. The small ON/OFF indicator indicates that either one of the following is large, that are the amount of increase of the electromyography per unit time from the offset section to the onset section, and the amount of decrease of the electromyography per unit time from the onset section to the offset section. The small ON/OFF indicator means that a time required for switching between the onset section and the offset section is small.

A large ON/OFF indicator means that the variation of the electromyography in the onset section is large. The large ON/OFF indicator indicates that the output of the electromyography is gentle, and the electromyography is high also when not necessary. The large ON/OFF indicator means that either one of the following is small, that are the amount of increase of the electromyography per unit time from the offset section to the onset section, and the amount of decrease of the electromyography per unit time from the onset section to the offset section. The large ON/OFF indicator means that the time required for switching between the onset section and the offset section is large.

As illustrated in FIG. 14, the ON/OFF indicator processing unit 25 may represent a time transition of the smoothed ON/OFF indicator calculated for each muscle and for each predetermined time with graphs. The ON/OFF indicator processing unit 25 may index the ON/OFF indicator with a score out of full score of 100 points. In a case of the ON/OFF indicator "0", the score is 100 points. The ON/OFF indicator processing unit 25 may index the score by the stepwise evaluation such as "Good", "Average", and "Bad". In a case of the ON/OFF indicator "0", the evaluation is "Good".

The ON/OFF indicator indexes the application of force to the muscle (on) at a necessary timing, and alternatively, the removal of the force from the muscle (off) at times other than the necessary timing. The ON/OFF indicator can urge an exercise that improves the agility of the ON/OFF switching of the muscles.

Another Embodiment of Balance Indicator Processing Unit

The balance indicator output by the balance indicator processing unit 28 is calculated based on the degree of synchronization of the transition of the electromyography of each of the muscles.

The synchronization of the transition of the electromyography indicates that the electromyography of each of the muscles increases or decreases in the same way. The balance indicator is calculated based on a degree of divergence of a differential value of the electromyography of each of the muscles at a predetermined time.

More specifically, the balance indicator processing unit 28 calculates the root-mean-square value of the electromyography for each predetermined time. The balance indicator processing unit 28 repeats a process of outputting, as a balance evaluation value of a predetermined muscle, a value acquired by subjecting, to time differentiation, the time course of the averaged value of the root-mean-square value in the sliding window for calculating balance evaluation value, for each of the pieces of electromyography data of each of the plurality of muscles. The balance indicator processing unit 28 outputs the balance indicator based on the balance evaluation value of each of the plurality of muscles.

The balance indicator processing unit 28 makes the calculation for the plurality of muscles at the predetermined time. The balance indicator processing unit 28 may calculate the balance indicator for each predetermined time and may output the transition of the balance indicator.

The balance indicator processing unit 28 outputs a balance indicator indicating that the balance of each of the muscles is inappropriate if the degree of synchronization of the transition of the electromyography of each of the muscles is low. For example, if the degree of divergence of the differential value of the electromyography of each of the muscles at the predetermined time is large, the balance indicator processing unit 28 determines that the degree of synchronization of the transition of the electromyography of each of the muscles at the predetermined time is low.

The balance indicator processing unit 28 outputs a balance indicator indicating that the balance of each of the muscles is appropriate if the degree of synchronization of the transition of the electromyography of each of the muscles is high. For example, if the degree of divergence of the differential value of the electromyography of each of the muscles at the predetermined time is small, the balance indicator processing unit 28 determines that the degree of synchronization of the transition of the electromyography of each of the muscles at the predetermined time is high.

The balance indicator processing unit 28 may represent the time transition of the balance indicator calculated for the plurality of muscles for each predetermined time with graphs. The balance indicator processing unit 28 may index the balance indicator with a score out of full score of 100 points. If the balance indicator indicates that the balance of each of the muscles is appropriate, the score is 100 points. The balance indicator processing unit 28 may index the score by the stepwise evaluation such as "Good," "Average," and "Bad." If the balance indicator indicates that the balance of each of the muscles is appropriate, the evaluation is "Good."

The balance indicator indexes that the electromyography of each of the muscles increases or decreases in the same way. The balance indicator can urge an exercise by which each of the muscles increases or decreases in the same way.

The electromyography processing apparatus 1 according to the embodiment of the present invention described above uses a general-purpose computer system including, for example, a CPU (Central Processing Unit, processor) 901, a memory 902, a storage 903 (HDD: Hard Disk Drive, and SSD: Solid State Drive), a communication device 904, an input device 905, and an output device 906. The CPU 901 is the processing device 20. The memory 902 and the storage 903 are the storage devices 10. In this computer system, by the CPU 901 executing a predetermined program loaded on the memory 902, individual functions of the electromyography processing apparatus 1 are realized.

The electromyography processing apparatus 1 may be implemented on a single computer or on a plurality of computers. The electromyography processing apparatus 1 may be a virtual machine implemented on the computer.

A program of the electromyography processing apparatus 1 can be stored in a computer-readable recording medium such as an HDD, SSD, USB (Universal Serial Bus) memory, CD (Compact Disc), DVD (Digital Versatile Disc), or delivered via a network.

Other Embodiment

Although the present invention has been described based on the embodiment of the present invention, the discussion and drawings forming a part of this disclosure should not be construed as limiting the invention. Various alternative embodiments, examples, and operational techniques will be apparent to those skilled in the art from this disclosure.

For example, the window width and the moving width of the sliding window represented in the embodiment of the present invention are examples, and a window width and a moving width are appropriately set depending on a competition, a trial technique, and the like.

It is needless to say that the present invention encompasses various embodiments and the like which are not described herein. Therefore, the technical scope of the present invention is determined only by the matters specifying the invention according to the claims which are appropriate from the above description.

EXPLANATION OF THE REFERENCE NUMERALS

1 Electromyography processing apparatus
2 Electrode
10 Storage device
11 Electromyography data
12 RMS data
13 Onset data
14 ON/OFF indicator data
15 ON/OFF indicator smoothed data
16 Balance evaluation value data
20 Processing device
21 Electromyography acquisition unit
22 Pre-processing unit
23 Onset detection unit
24 Threshold value determination unit
25 ON/OFF indicator processing unit
26 ON/OFF indicator calculation unit
27 ON/OFF indicator output unit
28 Balance indicator processing unit
29 Balance evaluation value calculation unit
30 Balance indicator output unit
901 CPU
902 Memory
903 Storage
904 Communication device
905 input device
906 Output device

The invention claimed is:

1. An electromyography processing apparatus comprising one or more processors configured to:
obtain, from an electrode coupled to a predetermined muscle of a user, electromyography data indicating a time course of an electromyography;
store the electromyography data of the predetermined muscle;
filter the electromyography data to identify a signal in the electromyography data generated by activation of the predetermined muscle of the user;
determine that a portion of the filtered signal is an onset portion based on the electromyography of a sliding window for the onset portion and a dynamic threshold value, wherein the onset portion represents an increase in use of the predetermined muscle of the user and wherein the one or more processors are further configured to calculate the dynamic threshold value based on the electromyography of a sliding window for the dynamic threshold value and the sliding window for the dynamic threshold value moves in correspondence with a movement of the sliding window for the onset portion.

2. The electromyography processing apparatus according to claim 1, wherein
the sliding window for the dynamic threshold value is set in accordance with the sliding window for the onset portion.

3. The electromyography processing apparatus according to claim 1, wherein the one or more processors are configured to:
calculate a root-mean-square value in the electromyography data for each predetermined time;
generate root-mean-square value data including the root-mean-square value for each predetermined time;
set a sliding window for onset detection to a predetermined time of the root-mean-square value data;
determine, if an average of the root-mean-square value in the sliding window is higher than a threshold value, that the predetermined time is the onset portion;
set a sliding window for the dynamic threshold value to the predetermined time; and
determine the dynamic threshold value based on the average of the root-mean-square value in the sliding window for threshold value detection.

4. The electromyography processing apparatus according to claim 1, wherein a time of the sliding window for threshold value detection is longer than a time of the sliding window for onset detection.

5. The electromyography processing apparatus according to claim 1, wherein the one or more processors are configured to determine a bias of the user using the predetermined muscle over another muscle of the user by determining the onset portion reflects increased usage of the predetermined muscle over the other muscle based on other electromyography data obtained from another electrode coupled to the other muscle.

6. The electromyography processing apparatus according to claim 1, wherein the one or more processors are configured to filter the electromyography data to identify the signal in the electromyography data generated by activation of the predetermined muscle of the user by (i) applying a bandpass filter to the electromyography data to remove data indicative of noise and (ii) applying a wiener filter to an output of the bandpass filter to identify the signal in the electromyography data.

7. An electromyography processing method comprising:
obtaining, from an electrode coupled to a predetermined muscle of a user, electromyography data indicating a time course of an electromyography;
storing the electromyography data of the predetermined muscle; and
filtering the electromyography data to identify a signal in the electromyography data generated by activation of the predetermined muscle of the user;
determining that a portion of the filtered signal is an onset portion based on the electromyography of a sliding window for the onset portion and a dynamic threshold value, wherein the onset portion represents an increase in use of the predetermined muscle of the user, and
wherein determining that the portion is the onset portion further comprises calculating the dynamic threshold value based on the electromyography of a sliding window for the dynamic threshold value in the electromyography data and the sliding window for the dynamic threshold value moves in correspondence with a movement of the sliding window for the onset portion.

8. One or more non-transitory computer-readable media comprising instructions stored thereon that are executable by one or more processing devices and upon such execution cause the one or more processing devices to perform operations comprising:

obtaining, from an electrode coupled to a predetermined muscle of a user, electromyography data indicating a time course of an electromyography;

storing the electromyography data of the predetermined muscle;

filtering the electromyography data to identify a signal in the electromyography data generated by activation of the predetermined muscle of the user;

determining that a portion of the filtered signal is an onset portion based on the electromyography of a sliding window for the onset portion and a dynamic threshold value, wherein the onset portion represents an increase in use of the predetermined muscle of the user, and wherein determining that the portion is the onset portion further comprises calculating the dynamic threshold value based on the electromyography of a sliding window for the dynamic threshold value in the electromyography data and the sliding window for the dynamic threshold value moves in correspondence with a movement of the sliding window for the onset portion.

* * * * *